US008821528B2

(12) United States Patent
McGuckin, Jr. et al.

(10) Patent No.: US 8,821,528 B2
(45) Date of Patent: *Sep. 2, 2014

(54) REMOVABLE VEIN FILTER

(75) Inventors: James F. McGuckin, Jr., Radnor, PA (US); Richard T. Briganti, Malvern, PA (US); Peter W. J. Hinchliffe, Downington, PA (US)

(73) Assignee: Rex Medical, L.P., Conshohocken, PA (US)

( * ) Notice: Subject to any disclaimer, the term of this patent is extended or adjusted under 35 U.S.C. 154(b) by 1721 days.

This patent is subject to a terminal disclaimer.

(21) Appl. No.: 10/899,471

(22) Filed: Jul. 26, 2004

(65) Prior Publication Data

US 2005/0055046 A1 Mar. 10, 2005

Related U.S. Application Data

(60) Division of application No. 09/911,097, filed on Jul. 23, 2001, now Pat. No. 6,783,538, which is a continuation-in-part of application No. 09/883,819, filed on Jun. 18, 2001, now Pat. No. 6,623,506, and a continuation-in-part of application No. 09/883,818, filed on Jun. 18, 2001, now Pat. No. 6,793,665.

(51) Int. Cl.
*A61M 29/00* (2006.01)
*A61F 2/01* (2006.01)

(52) U.S. Cl.
CPC .............. *A61F 2/01* (2013.01); *A61F 2230/008* (2013.01); *A61F 2002/011* (2013.01); *A61F 2230/0067* (2013.01); *A61F 2002/016* (2013.01); *A61F 2230/0006* (2013.01); *A61F 2230/0091* (2013.01); *A61F 2230/0078* (2013.01)
USPC ........................................ 606/200

(58) Field of Classification Search
CPC ........................................ A61F 2/01
USPC .................. 606/200, 113, 114, 127, 128, 159
See application file for complete search history.

(56) References Cited

U.S. PATENT DOCUMENTS 3,744,492 A 7/1973 Leibinsohn
3,952,747 A 4/1976 Kimmell, Jr.
(Continued)

FOREIGN PATENT DOCUMENTS

DE 3429850 2/1986
DE 19509464 6/1996
(Continued)

OTHER PUBLICATIONS

B. Braun Medical, Inc. Vena Tech™ Vena Cava Filters, Feb. 2000.
(Continued)

*Primary Examiner* — Darwin Erezo
*Assistant Examiner* — Lindsey Bachman
(74) *Attorney, Agent, or Firm* — Neil D. Gershon

(57) ABSTRACT

The present provides a removable vessel filter comprising a first and second filtering portion and a first and second anchoring portion, wherein a transverse dimension of the first filtering portion in an expanded configuration is less than a transverse dimension of the first anchoring portion in an expanded configuration, and a transverse dimension of the second filtering portion is less than a transverse dimension of the second anchoring portion. The first and second filtering portions are positioned closer to each other than the first and second anchoring portions, and the anchoring portions being formed on first and second opposite portions of the vessel filter. The vessel filter is removable from a vessel wall by engagement of either the first filtering portion or the second filtering portion.

15 Claims, 30 Drawing Sheets

(56) References Cited

U.S. PATENT DOCUMENTS

| | | | |
|---|---|---|---|
| 4,425,908 A * | 1/1984 | Simon | 128/899 |
| 4,494,531 A | 1/1985 | Gianturco | |
| 4,512,338 A | 4/1985 | Balko et al. | |
| 4,619,246 A * | 10/1986 | Molgaard-Nielsen et al. | 128/899 |
| 4,688,553 A | 8/1987 | Metals | |
| 4,727,873 A | 3/1988 | Mobin-Uddin | |
| 4,781,177 A | 11/1988 | Lebigot | |
| 4,793,348 A | 12/1988 | Palmaz | |
| 4,817,600 A | 4/1989 | Herms et al. | |
| 4,832,055 A * | 5/1989 | Palestrant | 128/899 |
| 4,957,501 A | 9/1990 | Lahille et al. | |
| 4,990,156 A | 2/1991 | Lefebvre | |
| 4,994,069 A | 2/1991 | Ritchart et al. | |
| 5,059,205 A | 10/1991 | El-Nounou et al. | |
| 5,133,733 A | 7/1992 | Rasmussen et al. | |
| 5,152,777 A | 10/1992 | Goldberg et al. | |
| 5,234,458 A * | 8/1993 | Metais | 606/200 |
| 5,300,086 A | 4/1994 | Gory et al. | |
| 5,324,304 A | 6/1994 | Rasmussen | |
| 5,344,427 A | 9/1994 | Cottenceau et al. | |
| 5,350,398 A | 9/1994 | Pavcnik et al. | |
| 5,370,657 A | 12/1994 | Irie | |
| 5,375,612 A | 12/1994 | Cottenceau et al. | |
| 5,382,261 A | 1/1995 | Palmaz | |
| 5,383,887 A | 1/1995 | Nadal | |
| 5,405,377 A | 4/1995 | Cragg | |
| 5,531,788 A | 7/1996 | Dibie et al. | |
| 5,591,197 A | 1/1997 | Orth et al. | |
| 5,601,595 A | 2/1997 | Smith | |
| 5,626,605 A | 5/1997 | Irie et al. | |
| 5,634,942 A | 6/1997 | Chevillon et al. | |
| 5,681,347 A | 10/1997 | Catheart et al. | |
| 5,683,411 A | 11/1997 | Kavteladze et al. | |
| 5,690,671 A | 11/1997 | McGurk et al. | |
| 5,709,704 A | 1/1998 | Nott et al. | |
| 5,725,552 A | 3/1998 | Kotula et al. | |
| 5,733,294 A * | 3/1998 | Forber et al. | 606/151 |
| 5,733,329 A | 3/1998 | Wallace et al. | |
| 5,746,767 A | 5/1998 | Smith | |
| 5,755,779 A | 5/1998 | Horiguchi | |
| 5,755,790 A | 5/1998 | Chevillon et al. | |
| 5,776,162 A | 7/1998 | Kleshinski | |
| 5,782,748 A | 7/1998 | Palmer et al. | |
| 5,795,322 A | 8/1998 | Boudewijn | |
| 5,800,457 A | 9/1998 | Gelbfish | |
| 5,810,874 A | 9/1998 | Lefebvre | |
| 5,836,968 A | 11/1998 | Simon et al. | |
| 5,853,420 A | 12/1998 | Chevillon et al. | |
| 5,893,869 A | 4/1999 | Barnhart et al. | |
| 5,895,398 A | 4/1999 | Wensel et al. | |
| 5,895,410 A | 4/1999 | Forber et al. | |
| 5,911,717 A | 6/1999 | Jacobsen et al. | |
| 5,938,683 A | 8/1999 | Lefebvre | |
| 5,968,071 A | 10/1999 | Chevillon et al. | |
| 5,976,172 A | 11/1999 | Homsma et al. | |
| 5,984,947 A * | 11/1999 | Smith | 606/200 |
| 6,007,558 A | 12/1999 | Ravenscroft et al. | |
| 6,013,093 A | 1/2000 | Nott et al. | |
| 6,042,598 A | 3/2000 | Tsugita et al. | |
| 6,059,825 A | 5/2000 | Hobbs et al. | |
| 6,063,113 A | 5/2000 | Kavteladze et al. | |
| 6,066,158 A | 5/2000 | Engelson et al. | |
| 6,080,178 A | 6/2000 | Meglin | |
| 6,093,196 A | 7/2000 | Okada | |
| 6,093,199 A | 7/2000 | Brown et al. | |
| 6,096,052 A | 8/2000 | Callister et al. | |
| 6,099,549 A | 8/2000 | Bosma et al. | |
| 6,117,154 A | 9/2000 | Barbut et al. | |
| 6,123,715 A | 9/2000 | Amplatz | |
| 6,126,673 A | 10/2000 | Kim et al. | |
| 6,146,404 A | 11/2000 | Kim et al. | |
| 6,152,946 A | 11/2000 | Broome et al. | |
| 6,165,179 A | 12/2000 | Cathcart et al. | |
| 6,165,198 A | 12/2000 | McGurk et al. | |
| 6,168,579 B1 | 1/2001 | Tsugita | |
| 6,168,603 B1 | 1/2001 | Leslie et al. | |
| 6,171,327 B1 | 1/2001 | Daniel et al. | |
| 6,171,328 B1 | 1/2001 | Addis | |
| 6,179,851 B1 | 1/2001 | Barbut et al. | |
| 6,179,859 B1 | 1/2001 | Bates et al. | |
| 6,187,025 B1 | 2/2001 | Machek | |
| 6,193,739 B1 | 2/2001 | Chevillon et al. | |
| 6,214,025 B1 | 4/2001 | Thistle et al. | |
| 6,217,600 B1 | 4/2001 | DiMatteo | |
| 6,231,581 B1 | 5/2001 | Shank et al. | |
| 6,231,589 B1 | 5/2001 | Wessman et al. | |
| 6,235,044 B1 | 5/2001 | Root et al. | |
| 6,235,045 B1 | 5/2001 | Barbut et al. | |
| 6,241,746 B1 | 6/2001 | Bosma et al. | |
| 6,245,012 B1 | 6/2001 | Kleshinski | |
| 6,251,122 B1 | 6/2001 | Tsukernik | |
| 6,258,026 B1 | 7/2001 | Ravenscroft et al. | |
| 6,267,776 B1 | 7/2001 | O'Connell | |
| 6,273,901 B1 | 8/2001 | Whitcher et al. | |
| 6,280,451 B1 | 8/2001 | Bates et al. | |
| 6,280,457 B1 | 8/2001 | Wallace et al. | |
| 6,290,721 B1 | 9/2001 | Heath | |
| 6,331,183 B1 * | 12/2001 | Suon | 606/200 |
| 6,331,184 B1 | 12/2001 | Abrams | |
| 6,342,062 B1 | 1/2002 | Suon et al. | |
| 6,342,063 B1 | 1/2002 | Devries et al. | |
| 6,344,041 B1 | 2/2002 | Kupiecki et al. | |
| 6,355,051 B1 | 3/2002 | Sisskind et al. | |
| 6,368,338 B1 | 4/2002 | Konya | |
| 6,402,771 B1 | 6/2002 | Palmer et al. | |
| 6,436,120 B1 | 8/2002 | Meglin | |
| 6,436,121 B1 | 8/2002 | Blom | |
| 6,443,971 B1 | 9/2002 | Boylan et al. | |
| 6,443,972 B1 | 9/2002 | Bosma et al. | |
| 6,447,530 B1 * | 9/2002 | Ostrovsky et al. | 606/200 |
| 6,447,531 B1 | 9/2002 | Amplatz | |
| 6,458,139 B1 | 10/2002 | Palmer et al. | |
| 6,468,290 B1 | 10/2002 | Weldon et al. | |
| 6,482,222 B1 | 11/2002 | Bruckheimer et al. | |
| 6,506,205 B2 | 1/2003 | Goldberg et al. | |
| 6,517,559 B1 | 2/2003 | O'Connell | |
| 6,527,962 B1 | 3/2003 | Nadal | |
| 6,537,294 B1 | 3/2003 | Boyle et al. | |
| 6,540,767 B1 * | 4/2003 | Walak et al. | 606/200 |
| 6,551,342 B1 | 4/2003 | Shen et al. | |
| 6,562,058 B2 | 5/2003 | Sequin et al. | |
| 6,599,307 B1 | 7/2003 | Huter | |
| 6,605,102 B1 * | 8/2003 | Mazzocchi et al. | 606/200 |
| 6,652,558 B2 | 11/2003 | Patel et al. | |
| 6,660,021 B1 | 12/2003 | Palmer et al. | |
| 6,932,831 B2 | 8/2005 | Forber | |
| 6,989,021 B2 | 1/2006 | Bosma et al. | |
| 6,994,092 B2 | 2/2006 | Van der Burg | |
| 7,011,094 B2 | 3/2006 | Rapacki et al. | |
| 7,572,289 B2 | 8/2009 | Sisken et al. | |
| 7,704,266 B2 | 4/2010 | Thinnes et al. | |
| 7,875,018 B2 | 1/2011 | Tockman et al. | |
| 8,029,529 B1 | 10/2011 | Chanduszko | |
| 2002/0058911 A1 | 5/2002 | Gilson et al. | |
| 2002/0116024 A1 | 8/2002 | Goldberg et al. | |
| 2003/0065345 A1 | 4/2003 | Weadock | |
| 2003/0195555 A1 | 10/2003 | Khairkhahan et al. | |
| 2003/0208227 A1 | 11/2003 | Thomas | |
| 2003/0208253 A1 | 11/2003 | Beyer et al. | |
| 2004/0186556 A1 | 9/2004 | Hogendijk et al. | |
| 2005/0043757 A1 | 2/2005 | Arad et al. | |
| 2005/0165442 A1 | 7/2005 | Thinnes et al. | |
| 2005/0267515 A1 | 12/2005 | Oliva et al. | |
| 2005/0277977 A1 | 12/2005 | Thornton | |
| 2006/0095068 A1 | 5/2006 | WasDyke et al. | |
| 2006/0149295 A1 | 7/2006 | Fleming, III | |
| 2007/0173885 A1 | 7/2007 | Cartier et al. | |
| 2010/0049238 A1 | 2/2010 | Simpson | |
| 2010/0106178 A1 | 4/2010 | Obermiller et al. | |

(56) References Cited

U.S. PATENT DOCUMENTS

FOREIGN PATENT DOCUMENTS

| | | |
|---|---|---|
| EP | 1707233 | 10/2006 |
| FR | 2567405 | 7/1986 |
| WO | WO 9312723 | 7/1993 |
| WO | WO 9509567 | 4/1995 |
| WO | WO 9925252 | 5/1999 |
| WO | WO 0145590 | 6/2001 |
| WO | WO 0162184 | 8/2001 |
| WO | WO 0172239 | 10/2001 |
| WO | 0211812 | 2/2002 |
| WO | WO 0232496 | 4/2002 |
| WO | 2005 034764 | 4/2005 |

OTHER PUBLICATIONS

Gianturco-Roehm, Bird's Nest® Vena Cava Filter.
Cordis Corporation, TrapEase™ Permanent Vena Cava Filter, "A Small, Easy and Verstaile System for Optimal Pulmonary Emboli Preventation", 2000 (4 pages).

* cited by examiner

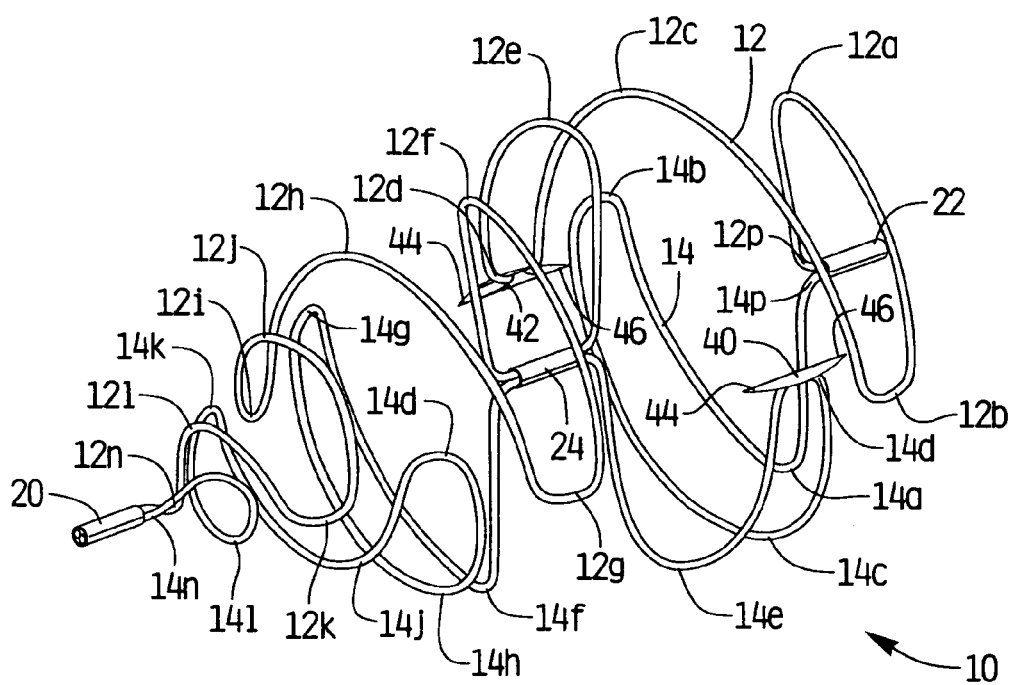
FIG_1
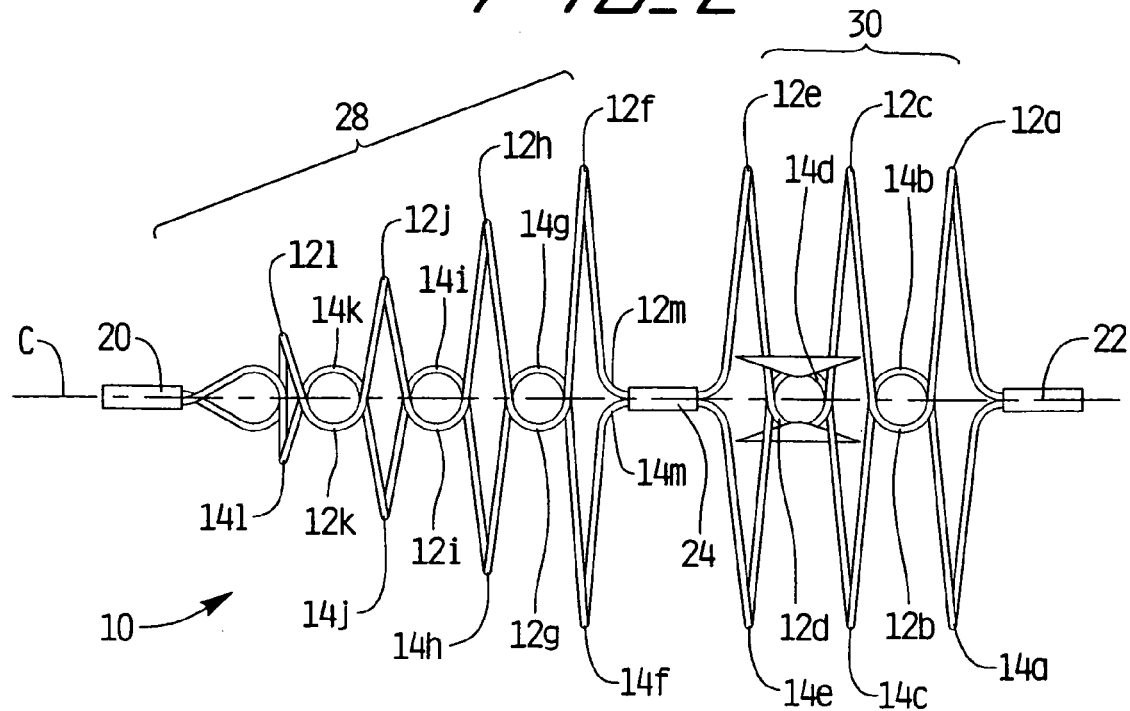
FIG_2

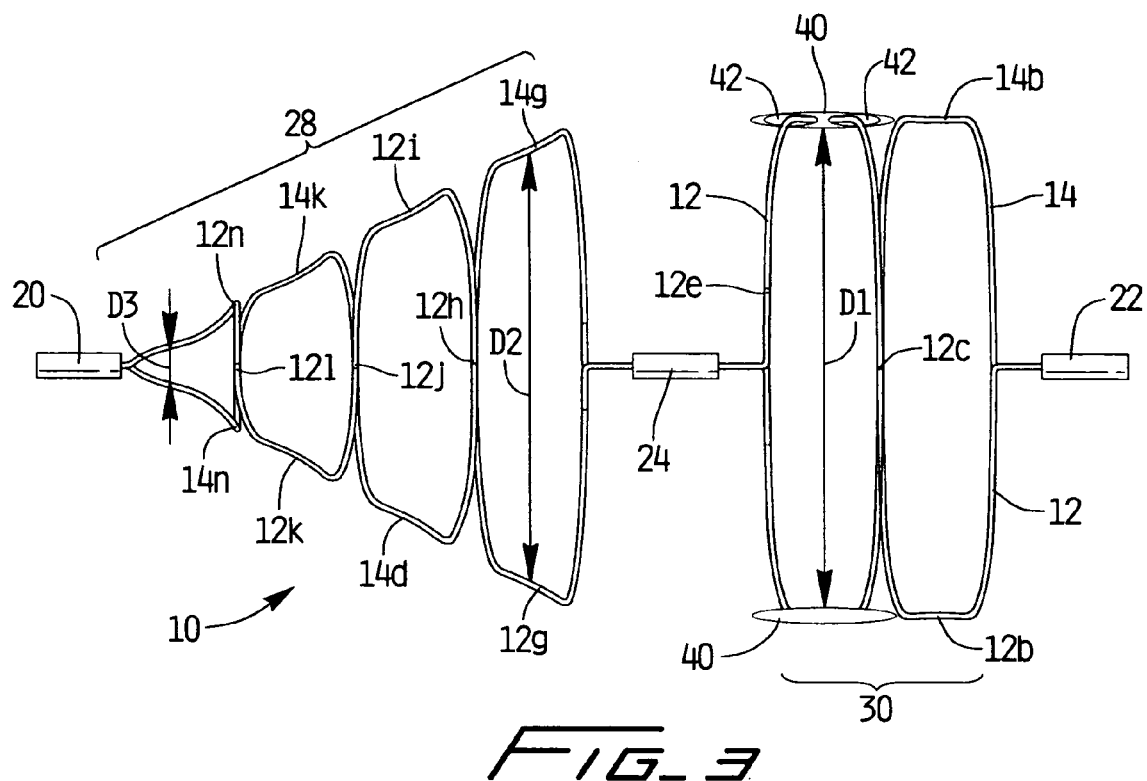
FIG_3
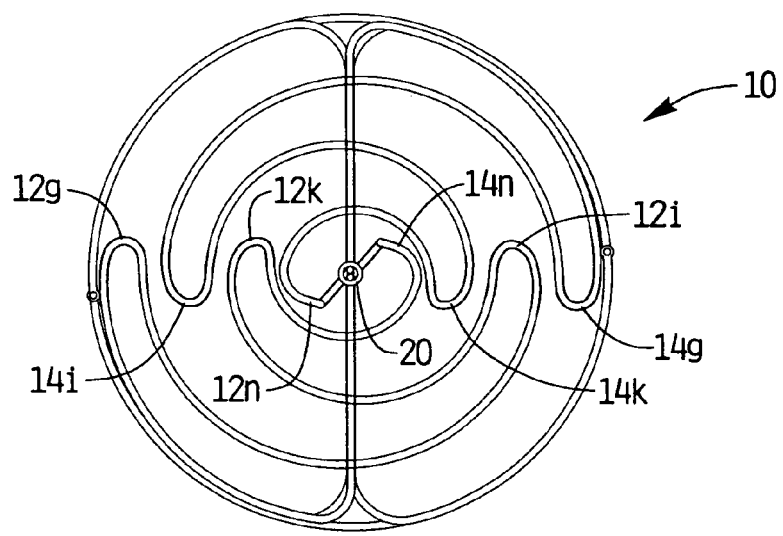
FIG_4

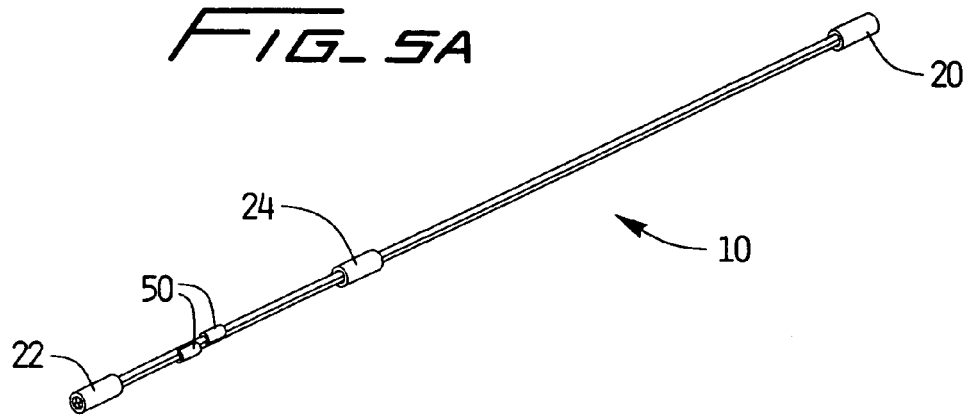
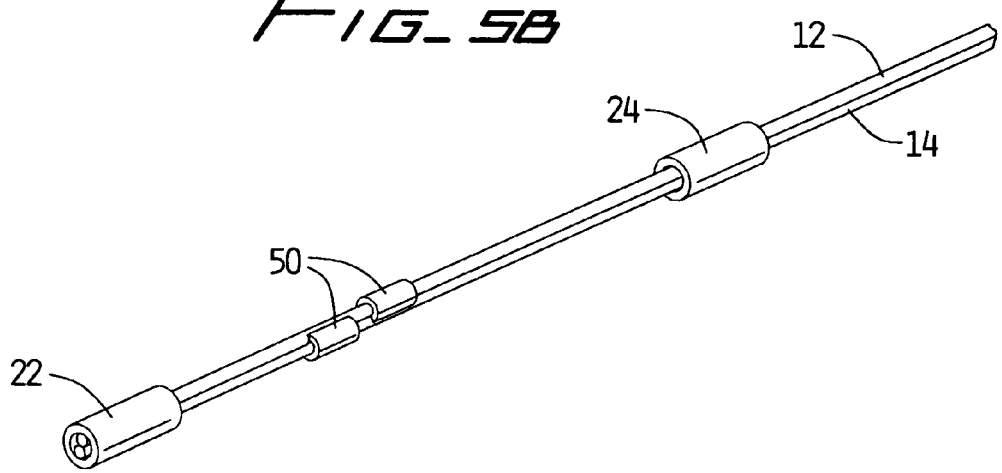
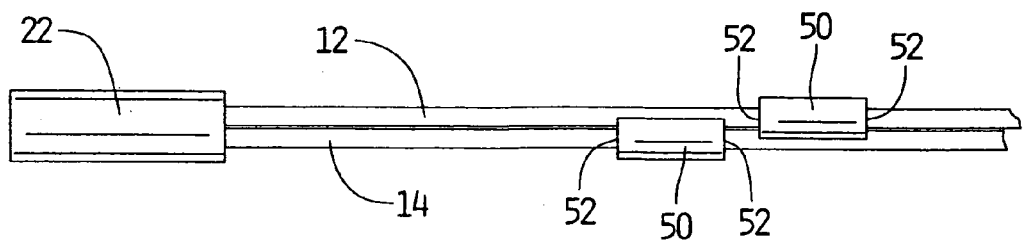

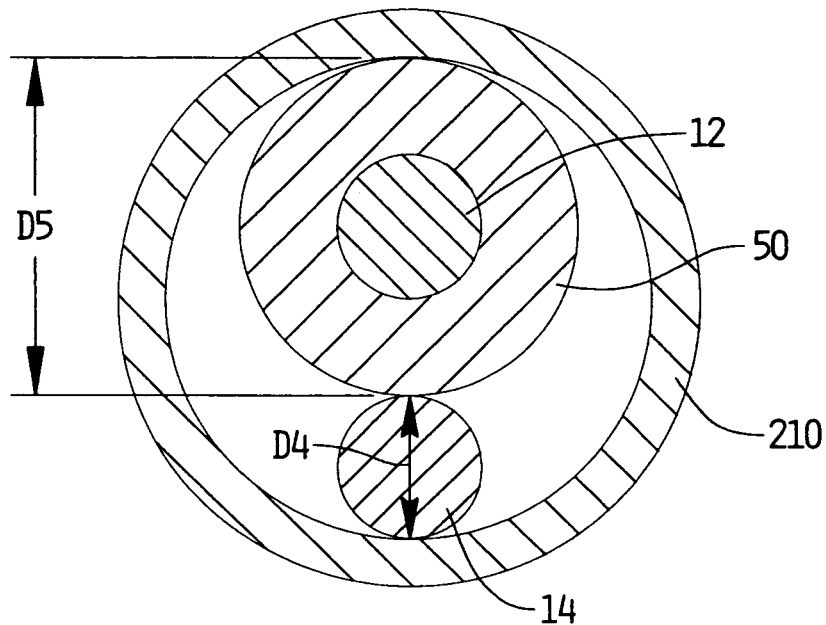
FIG_6A
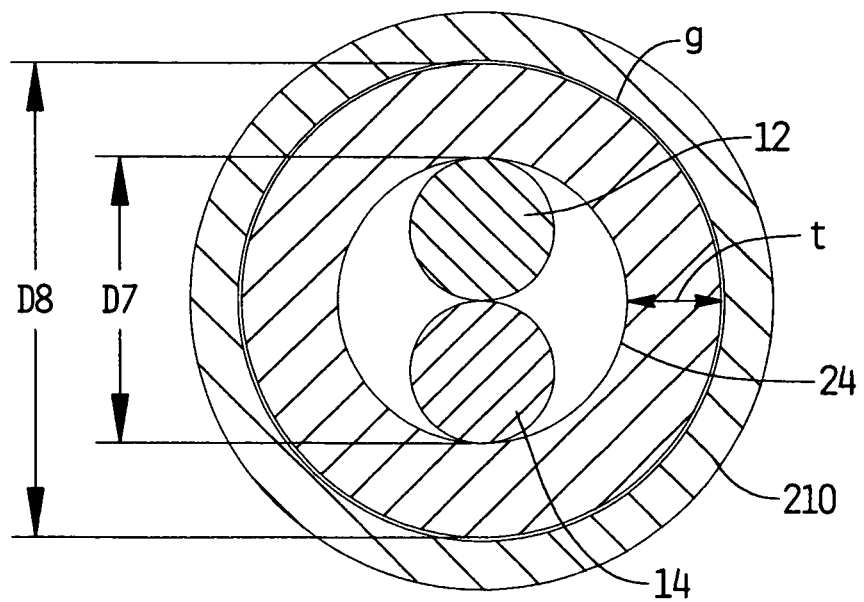
FIG_6B

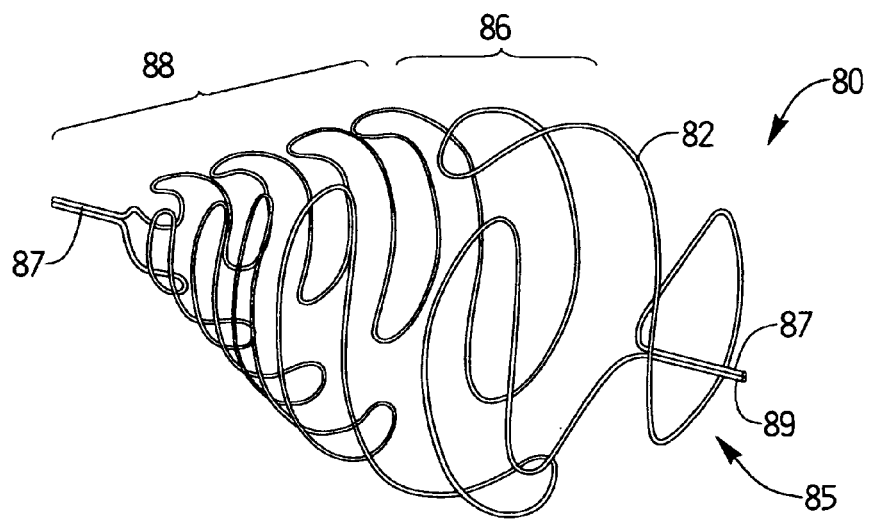
FIG_7
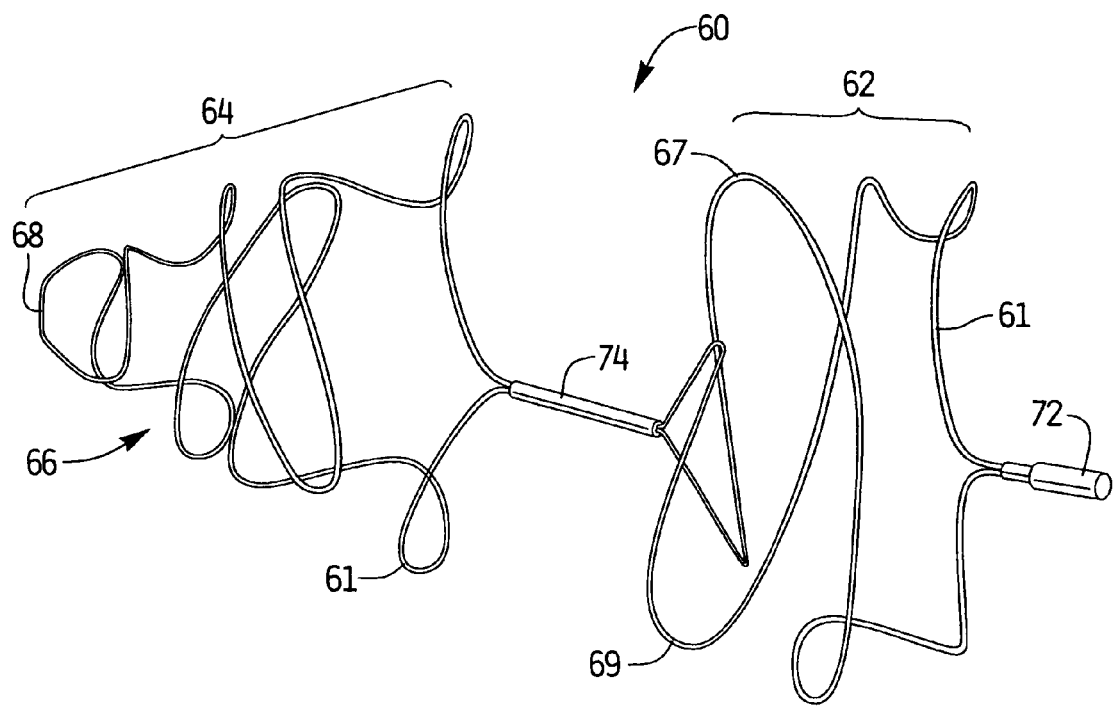
FIG_8

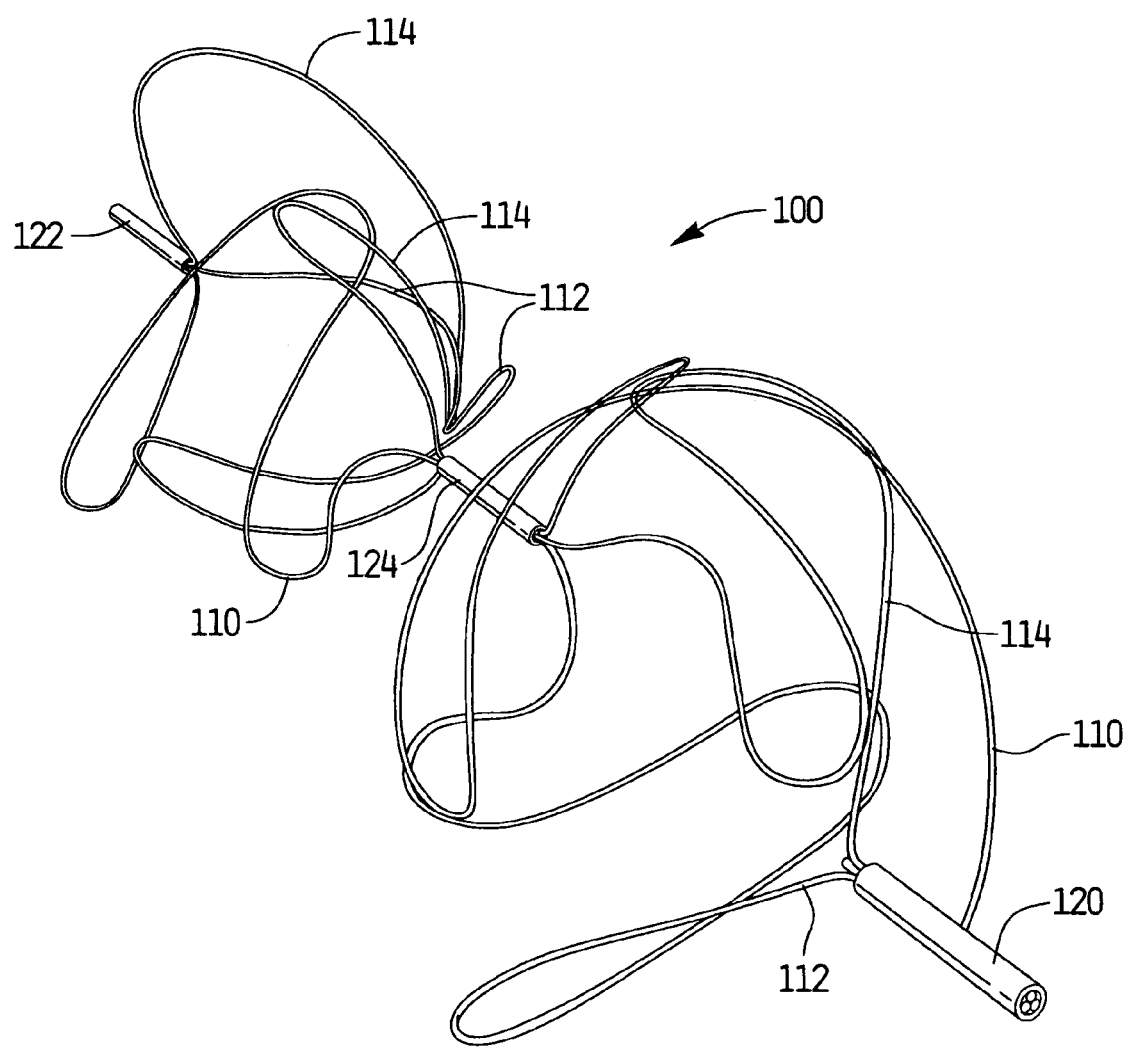

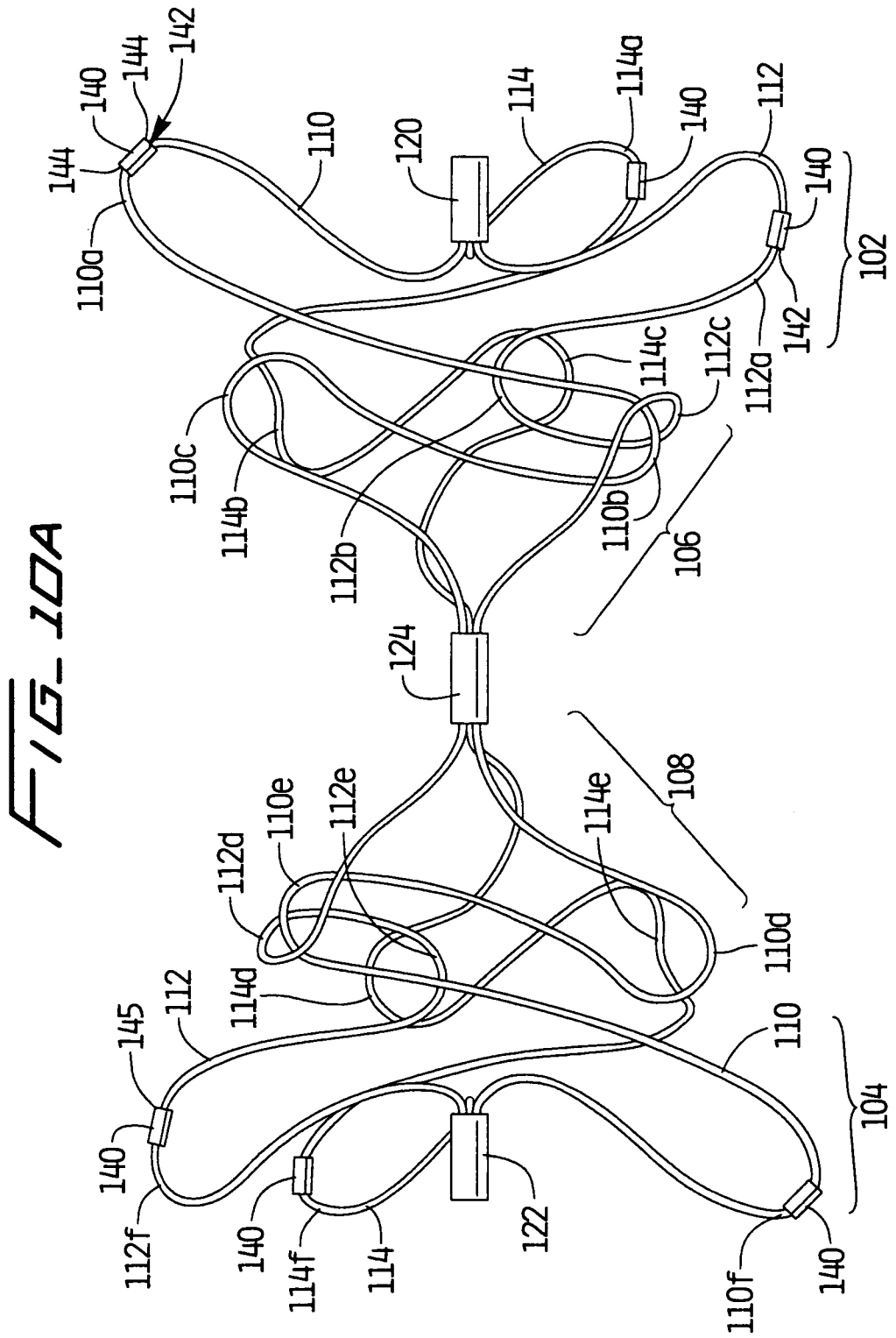

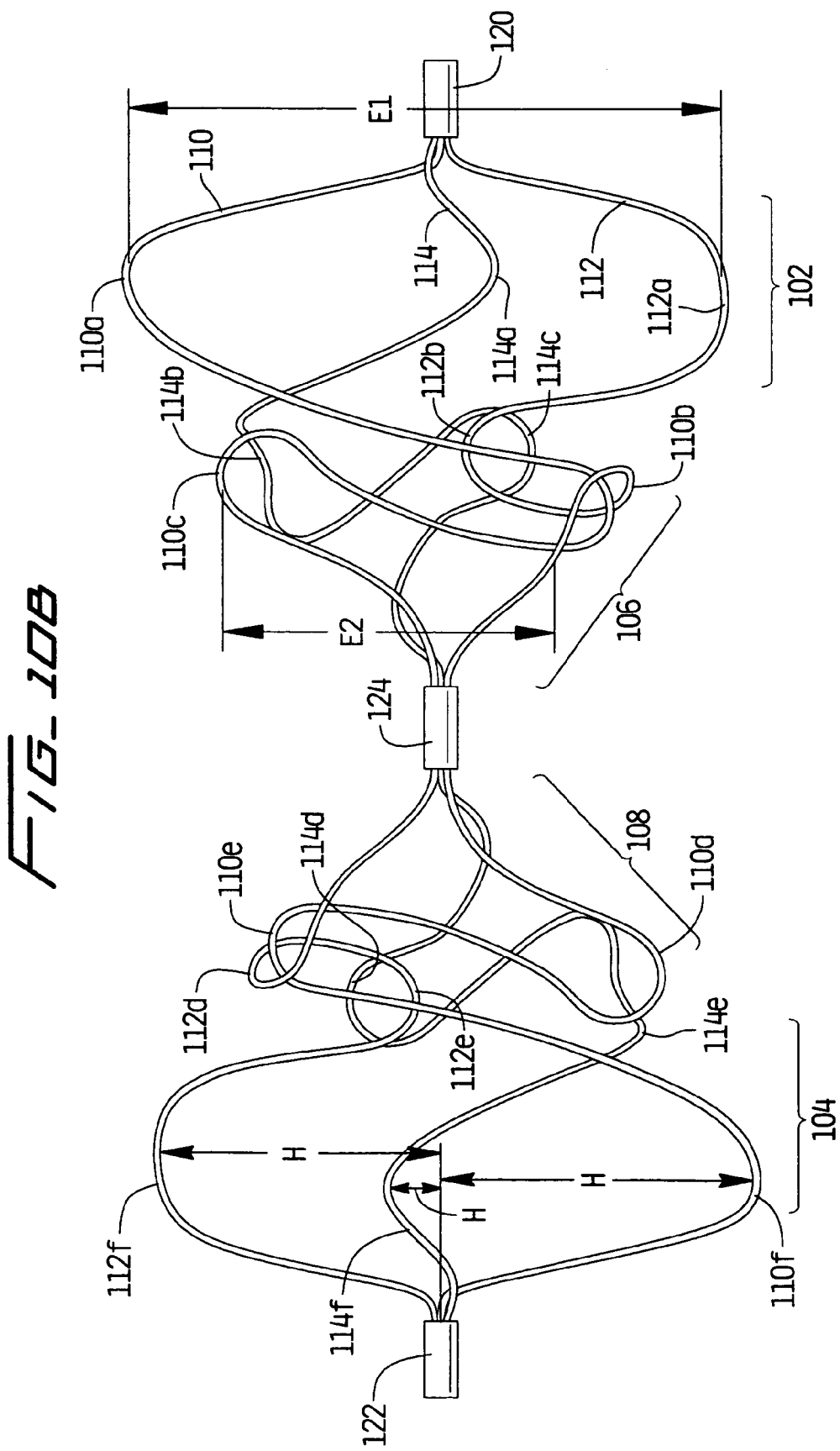

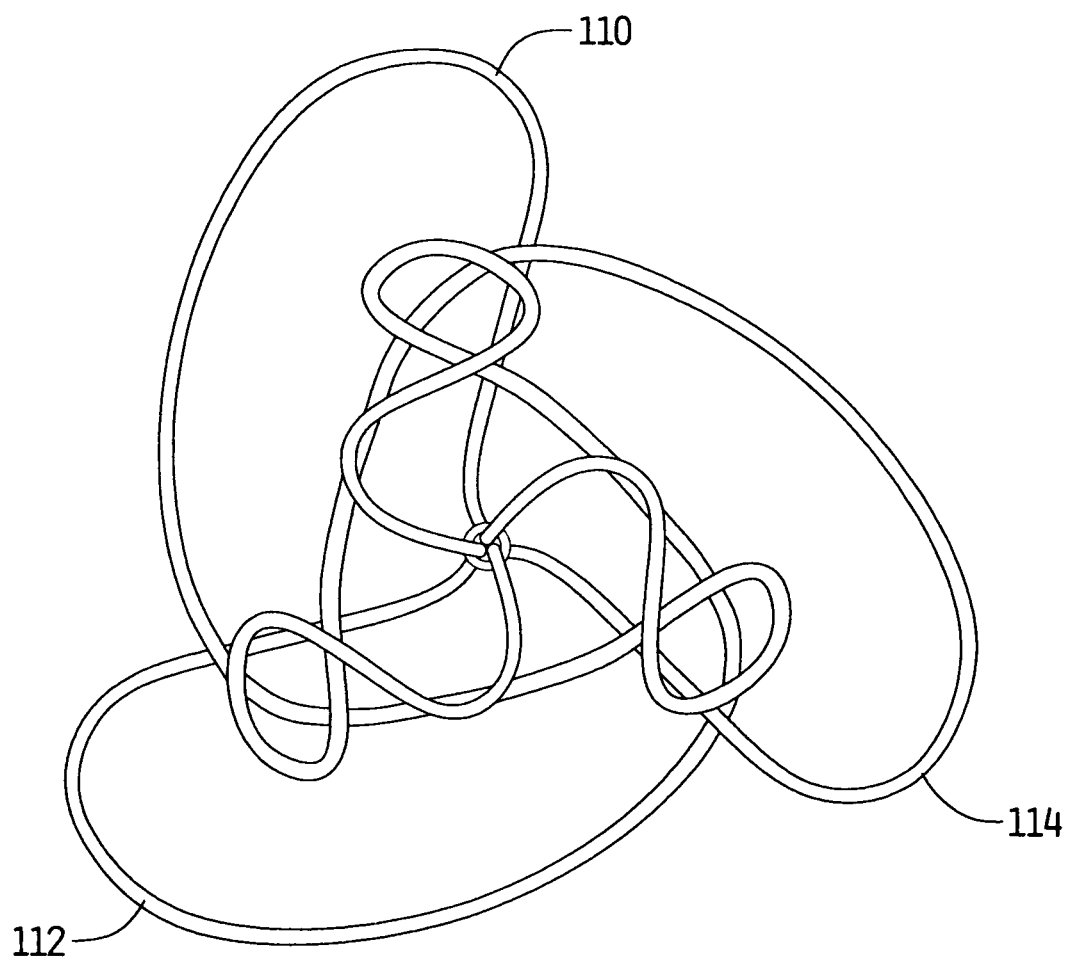
FIG_11

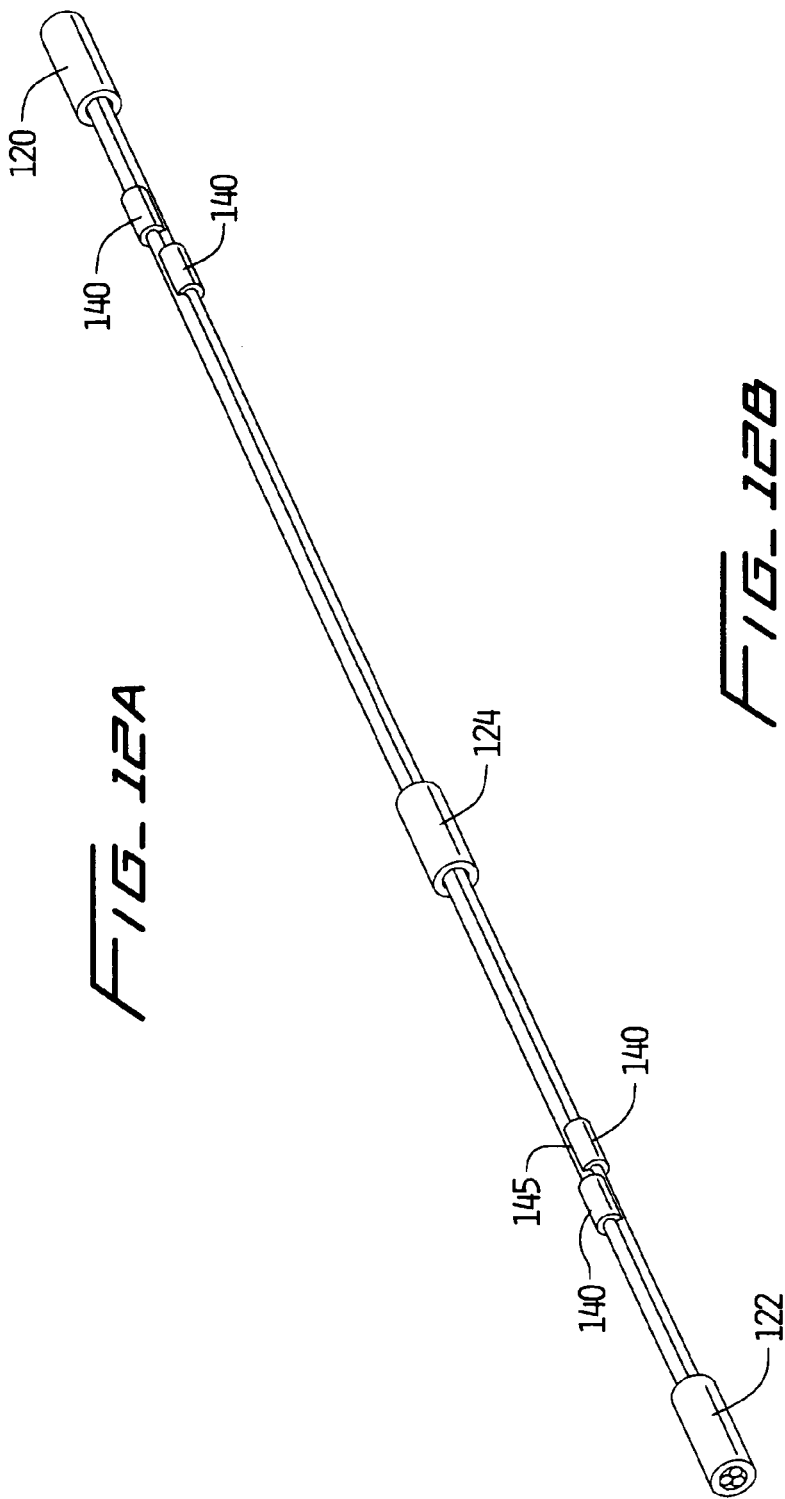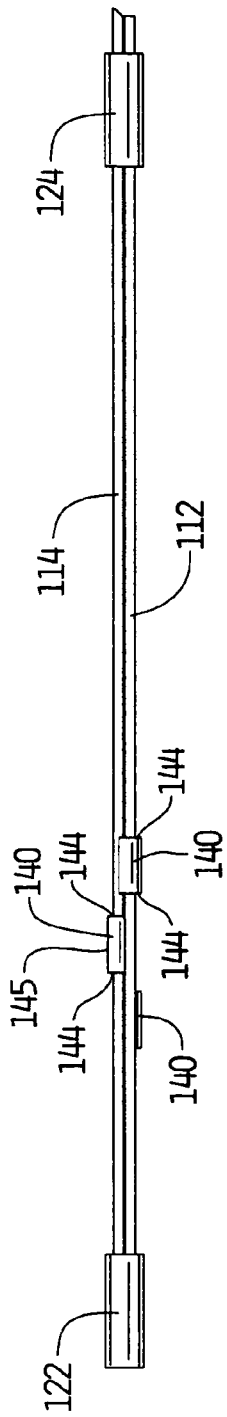

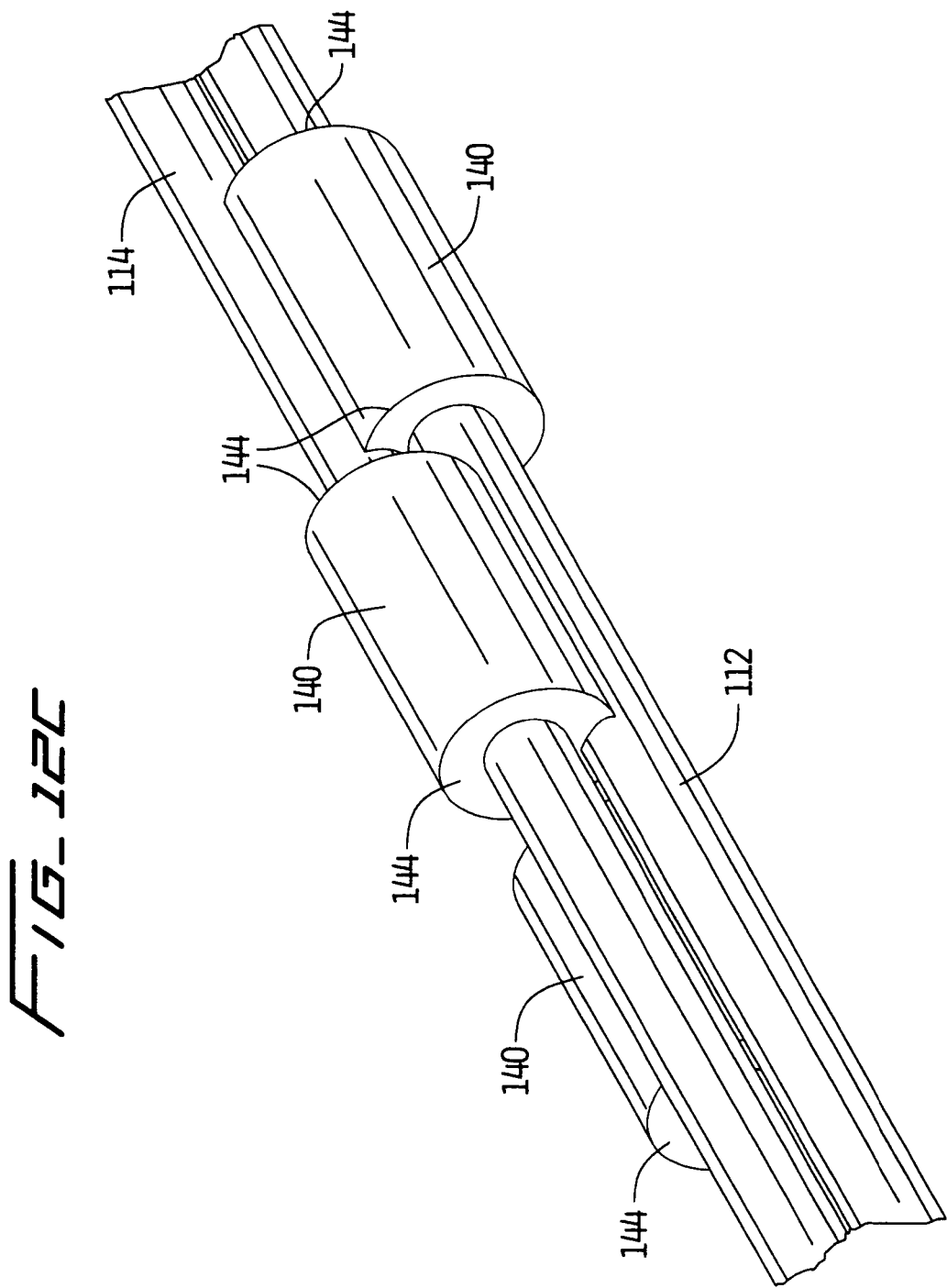

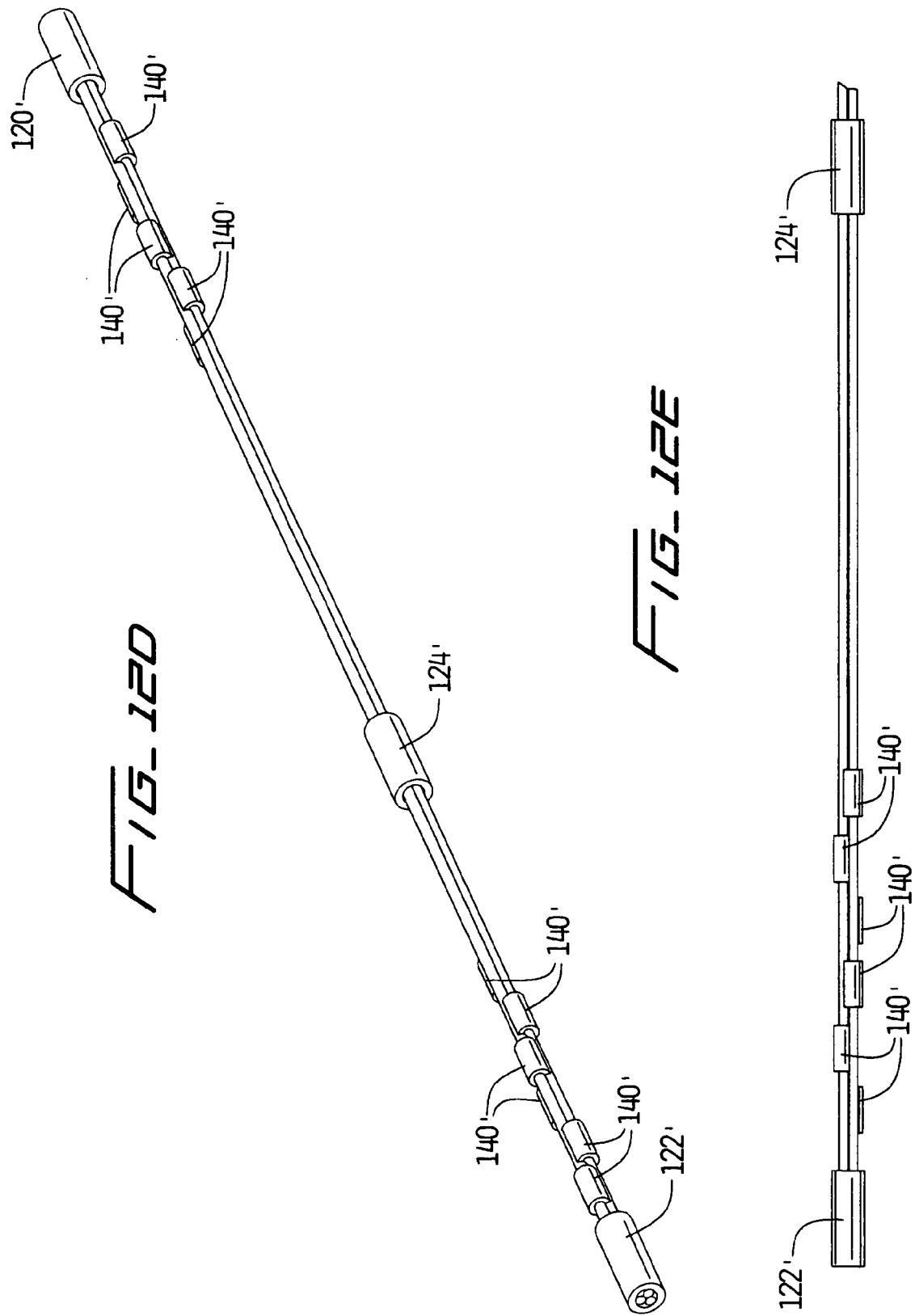

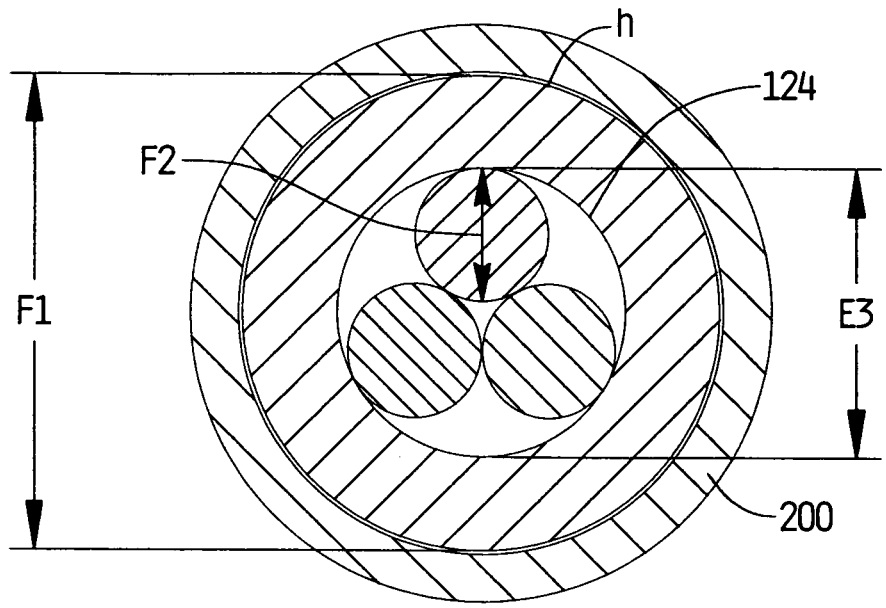
FIG_13A
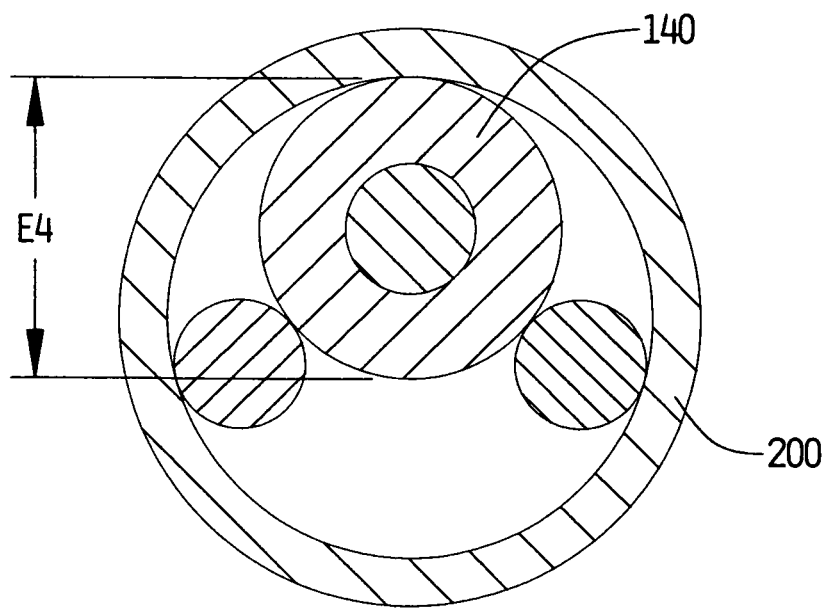
FIG_13B

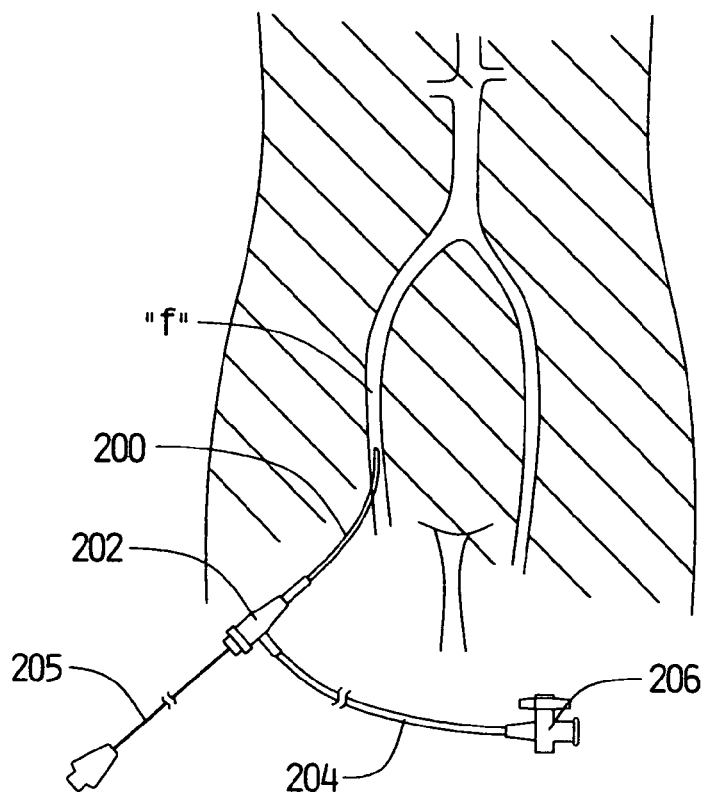
FIG_14
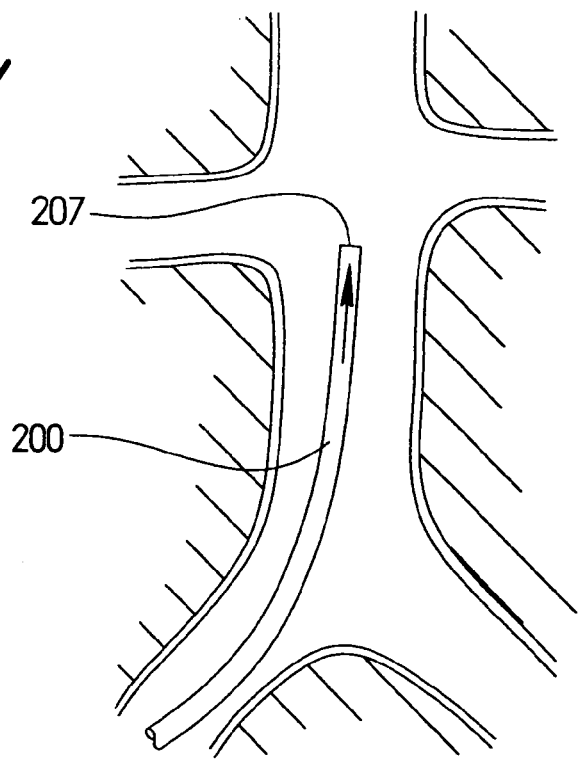
FIG_15

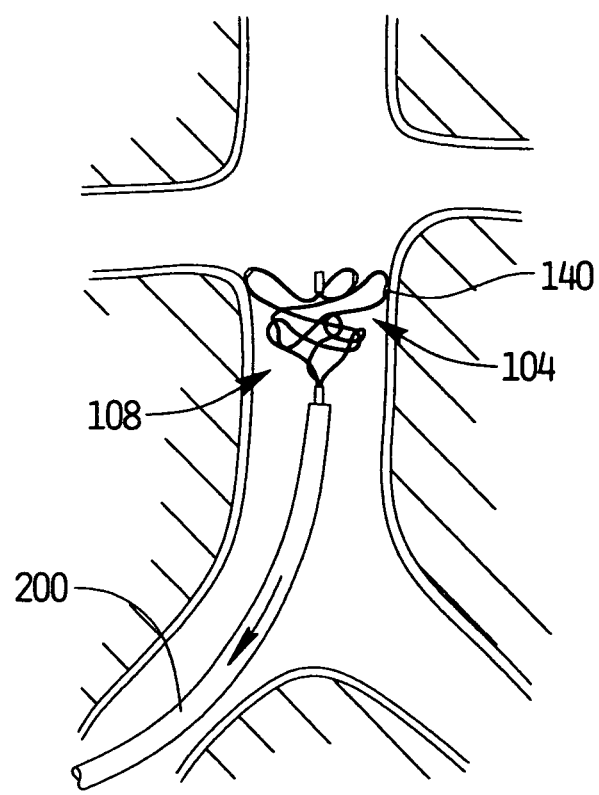
FIG_16

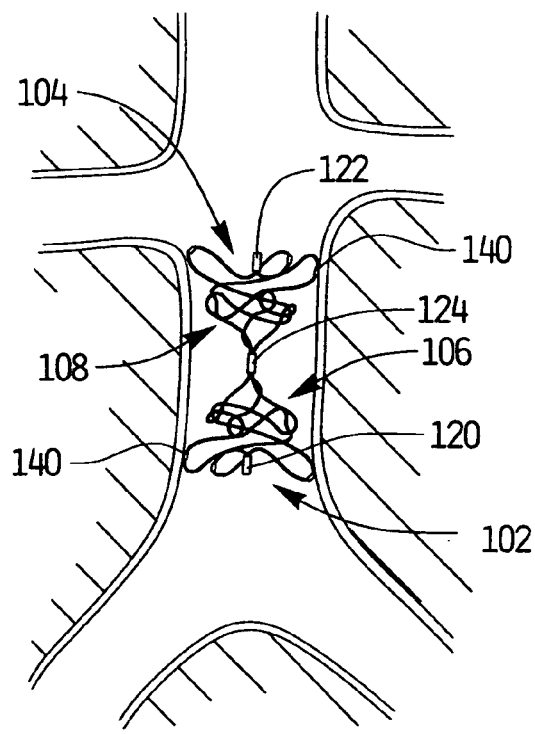
FIG_17
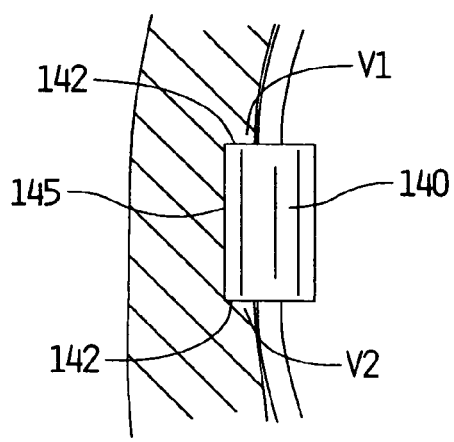
FIG_19
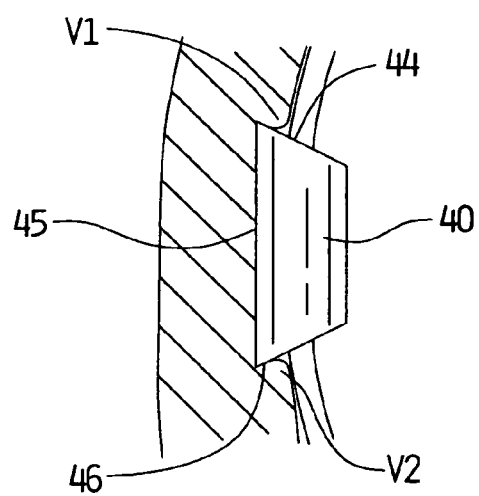
FIG_20

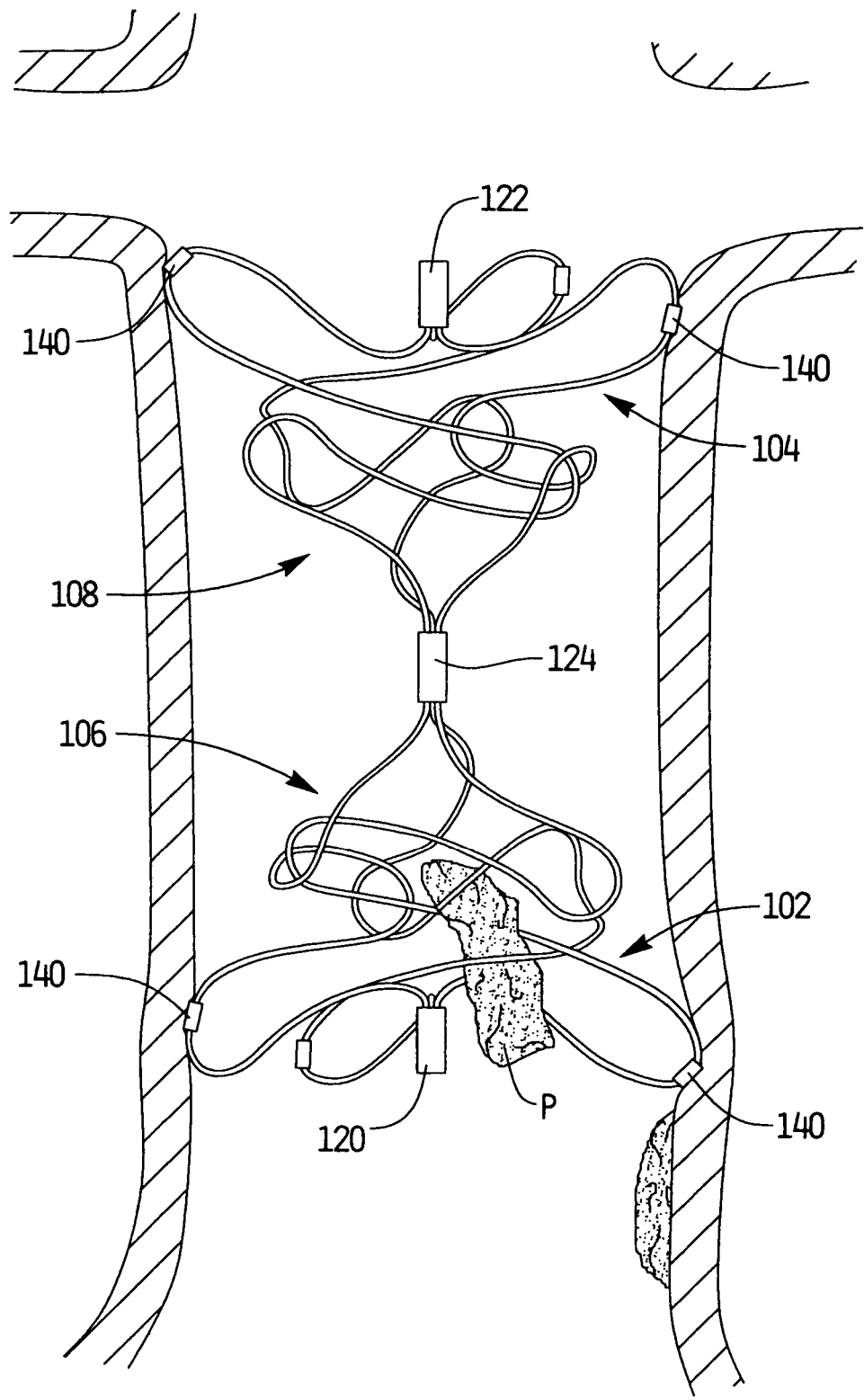
FIG_18A

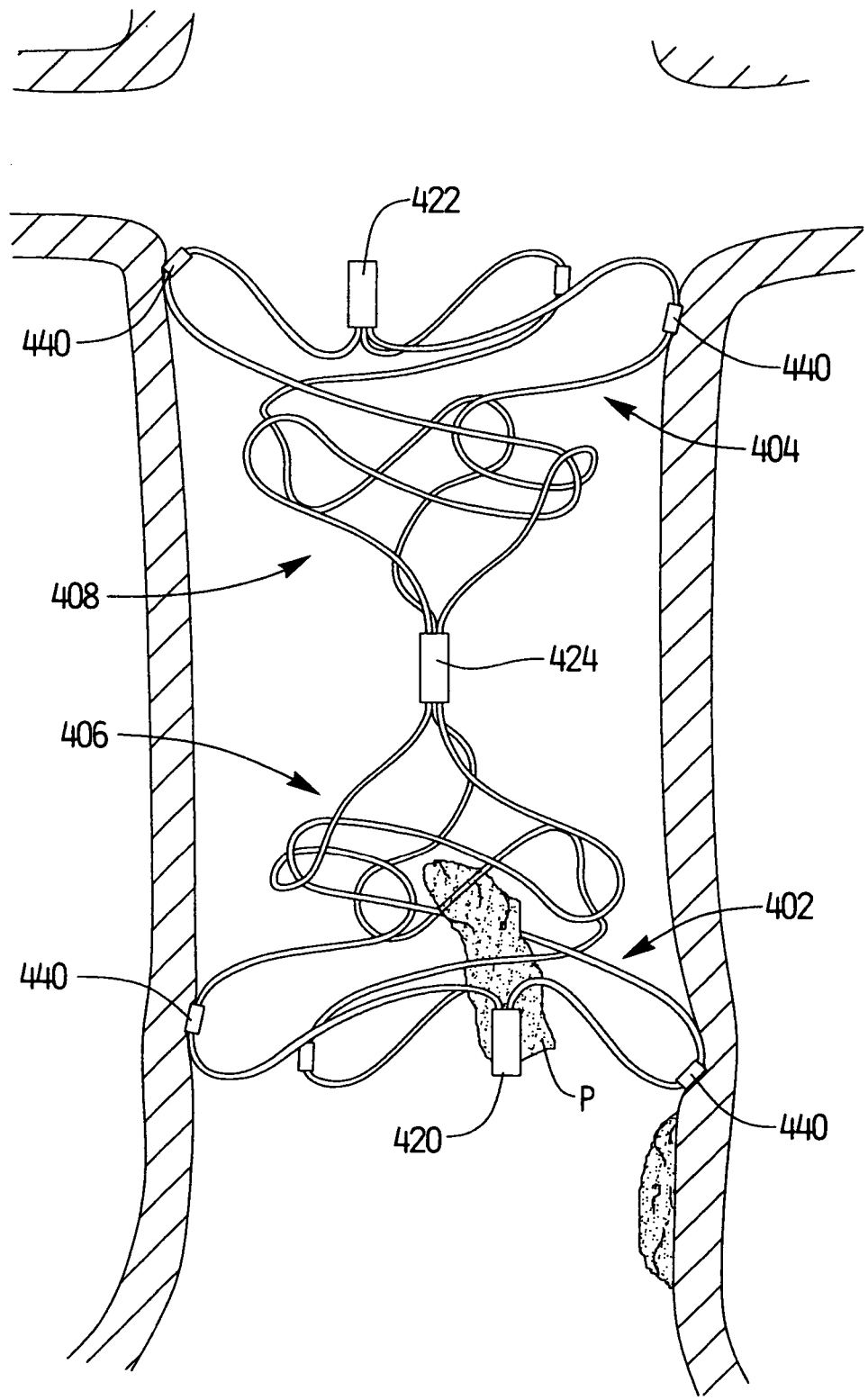
FIG_18B

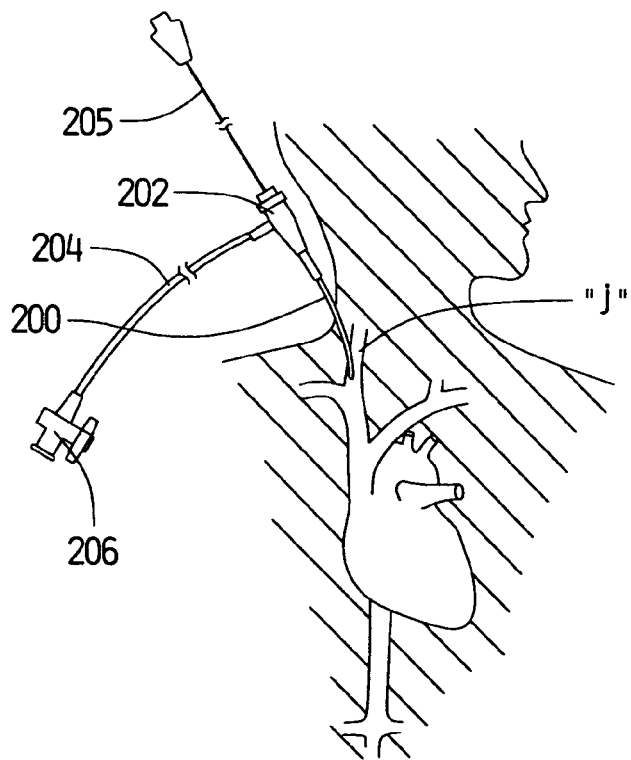
FIG_21
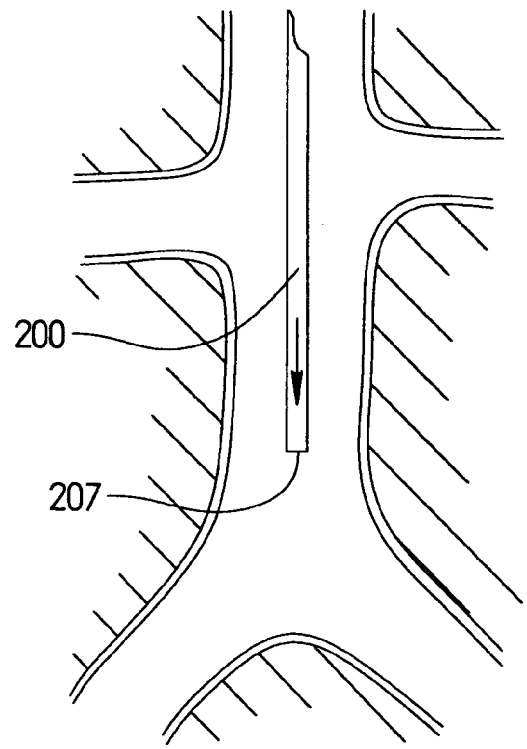
FIG_22

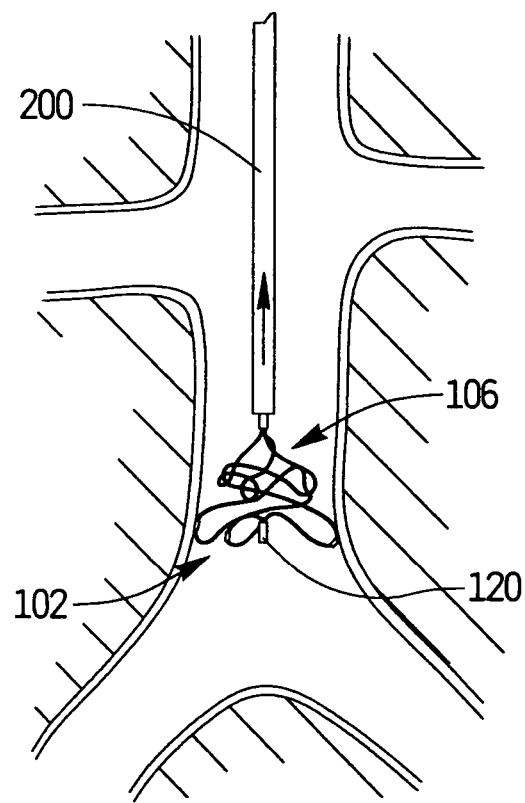
FIG_23

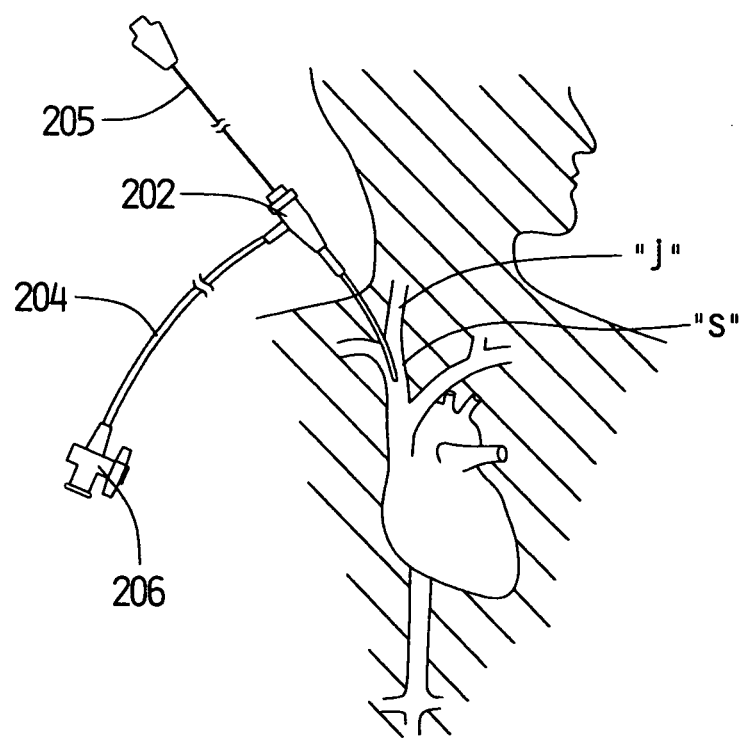
FIG_24

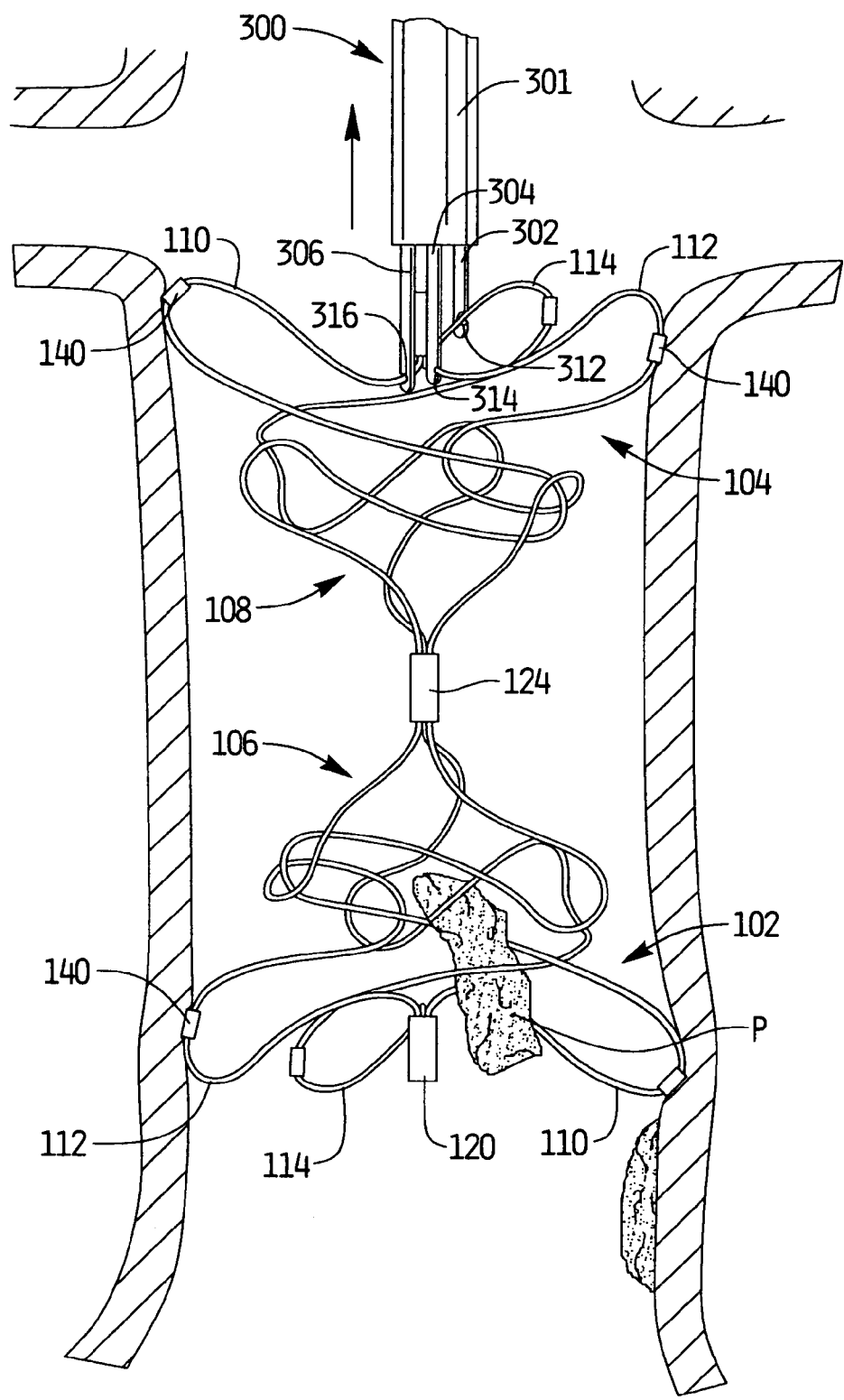
FIG_25

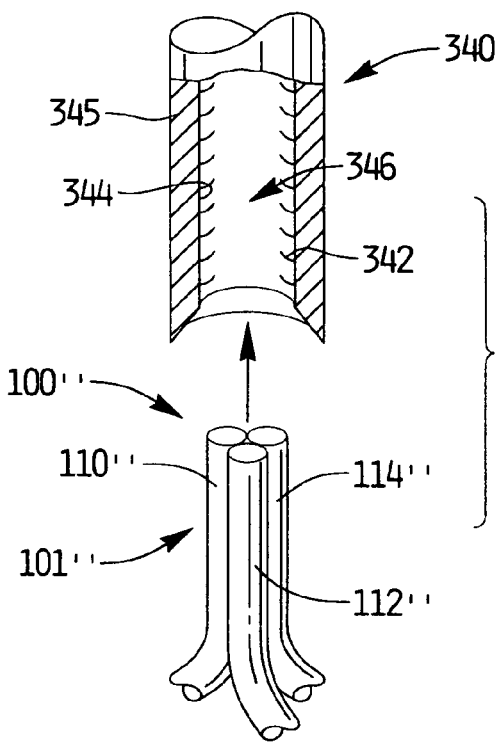
FIG_26A
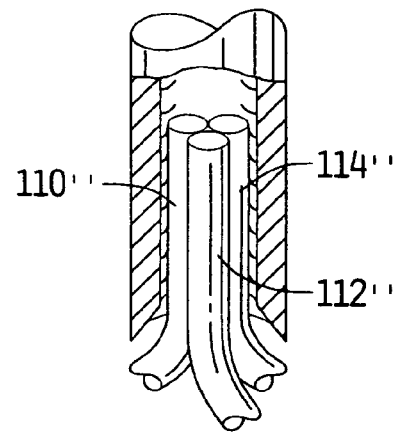
FIG_26B
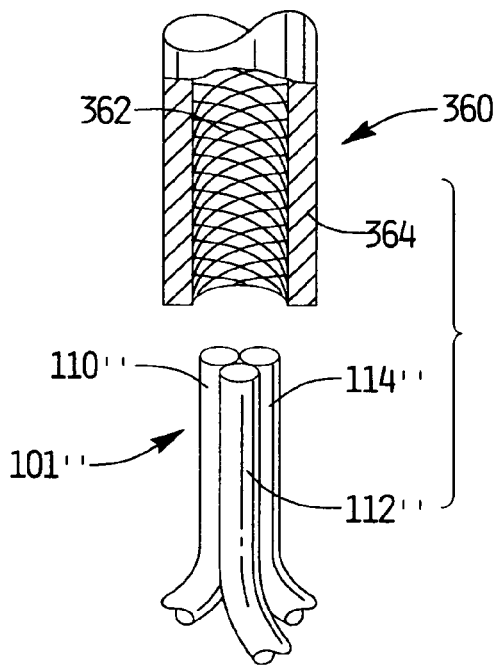
FIG_27A
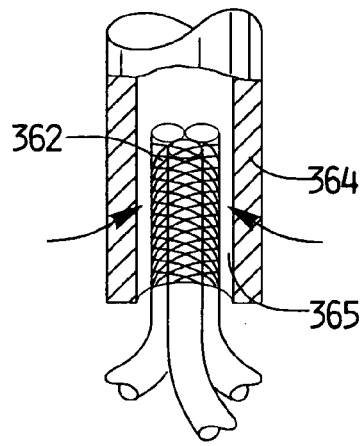
FIG_27B

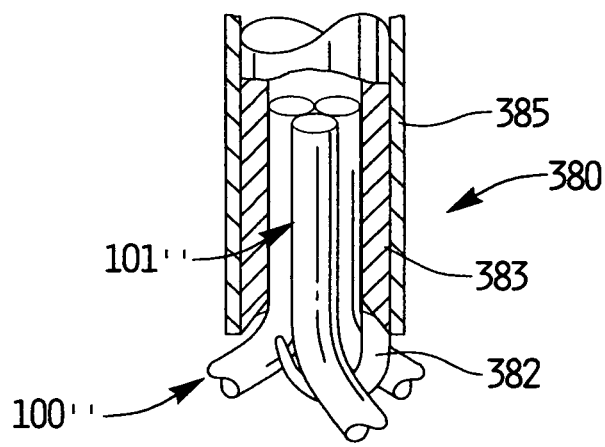
FIG_28
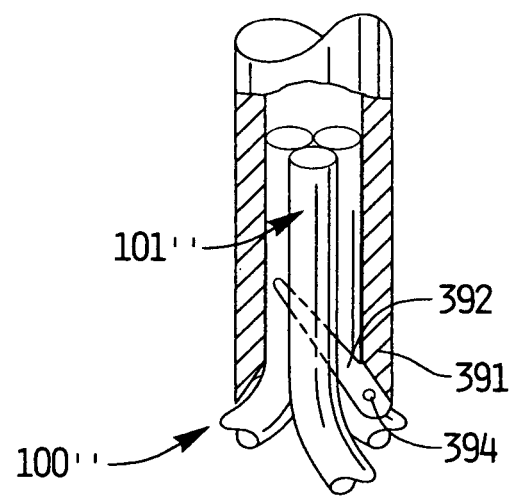
FIG_29

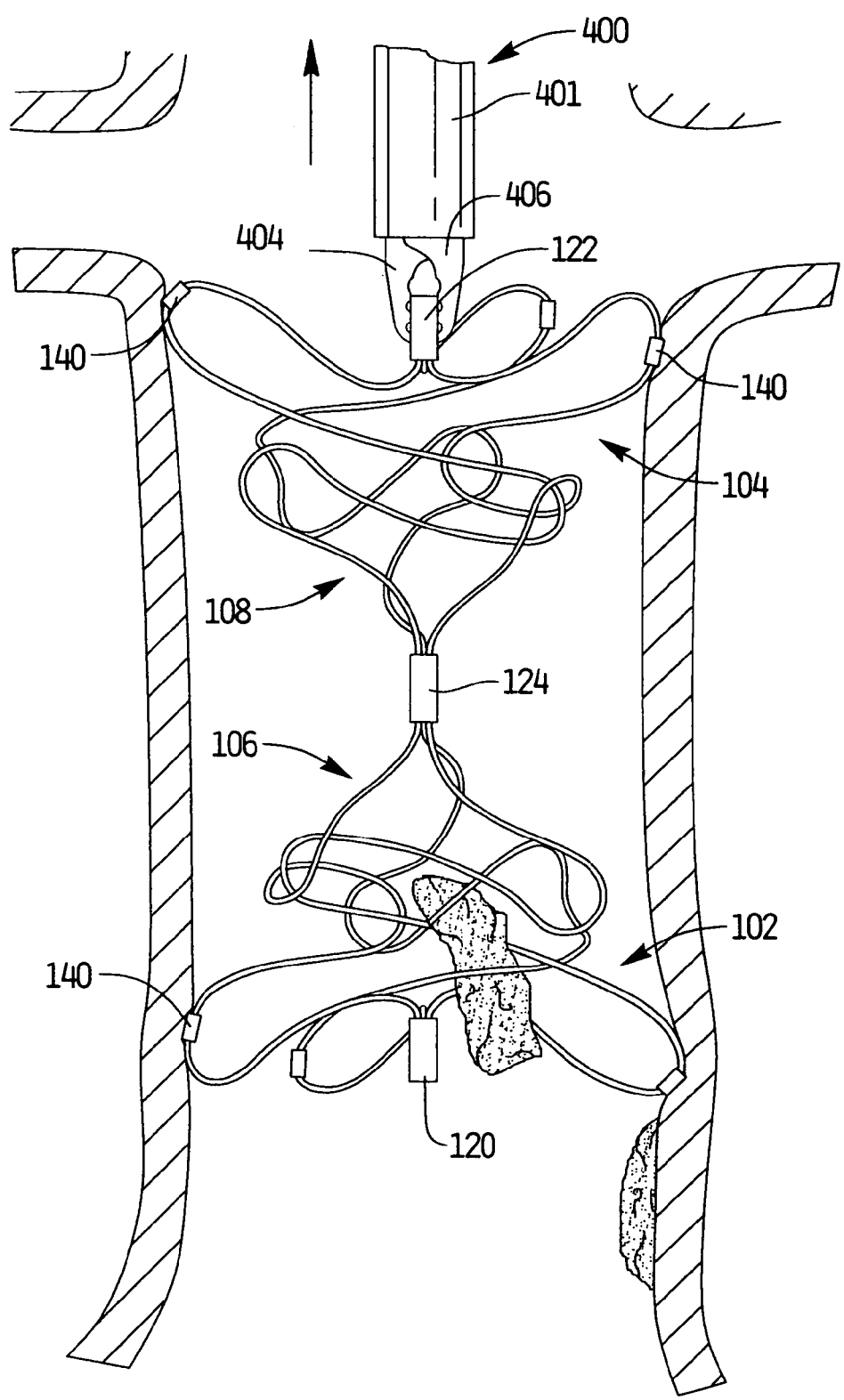
FIG_30

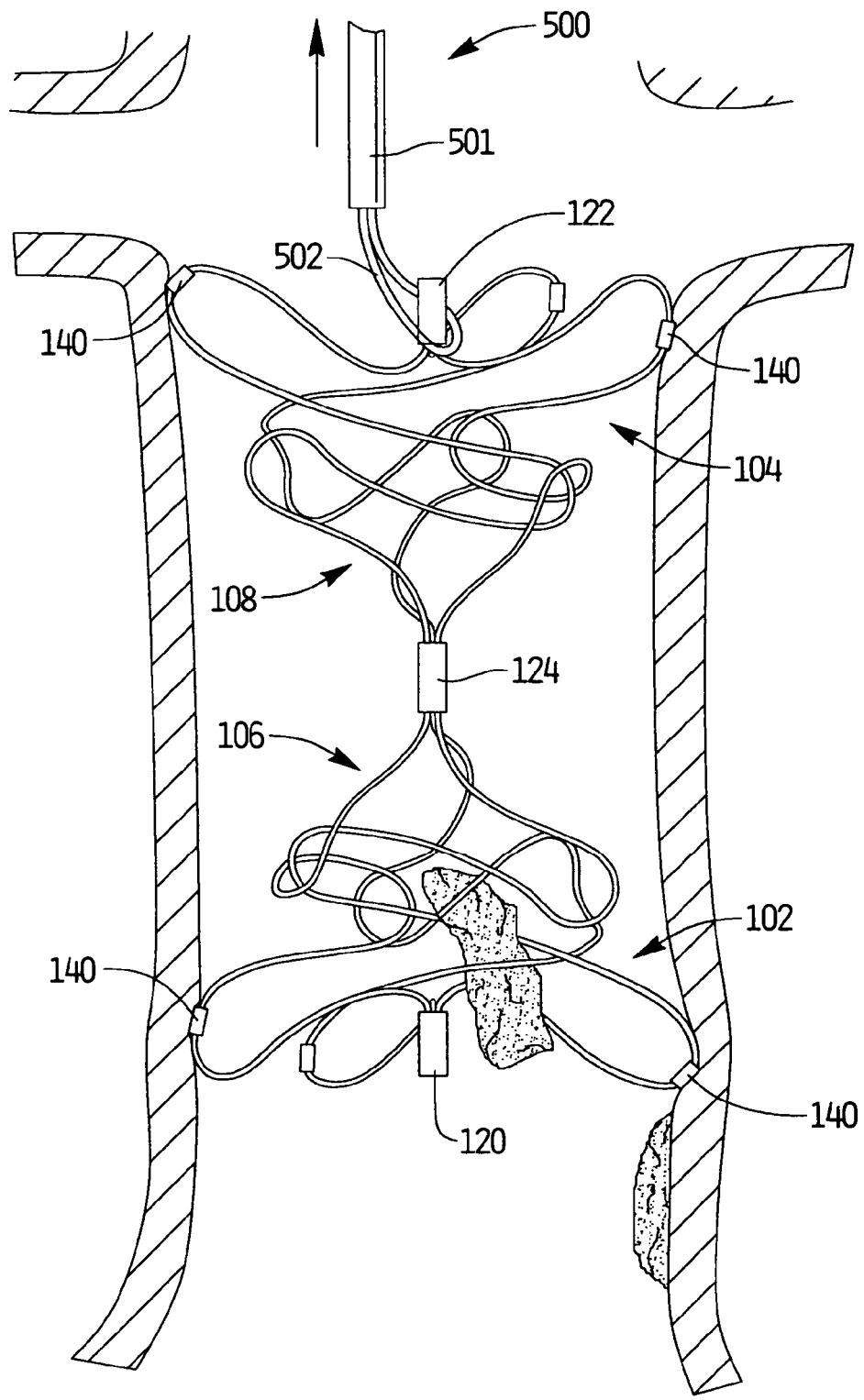
FIG_31

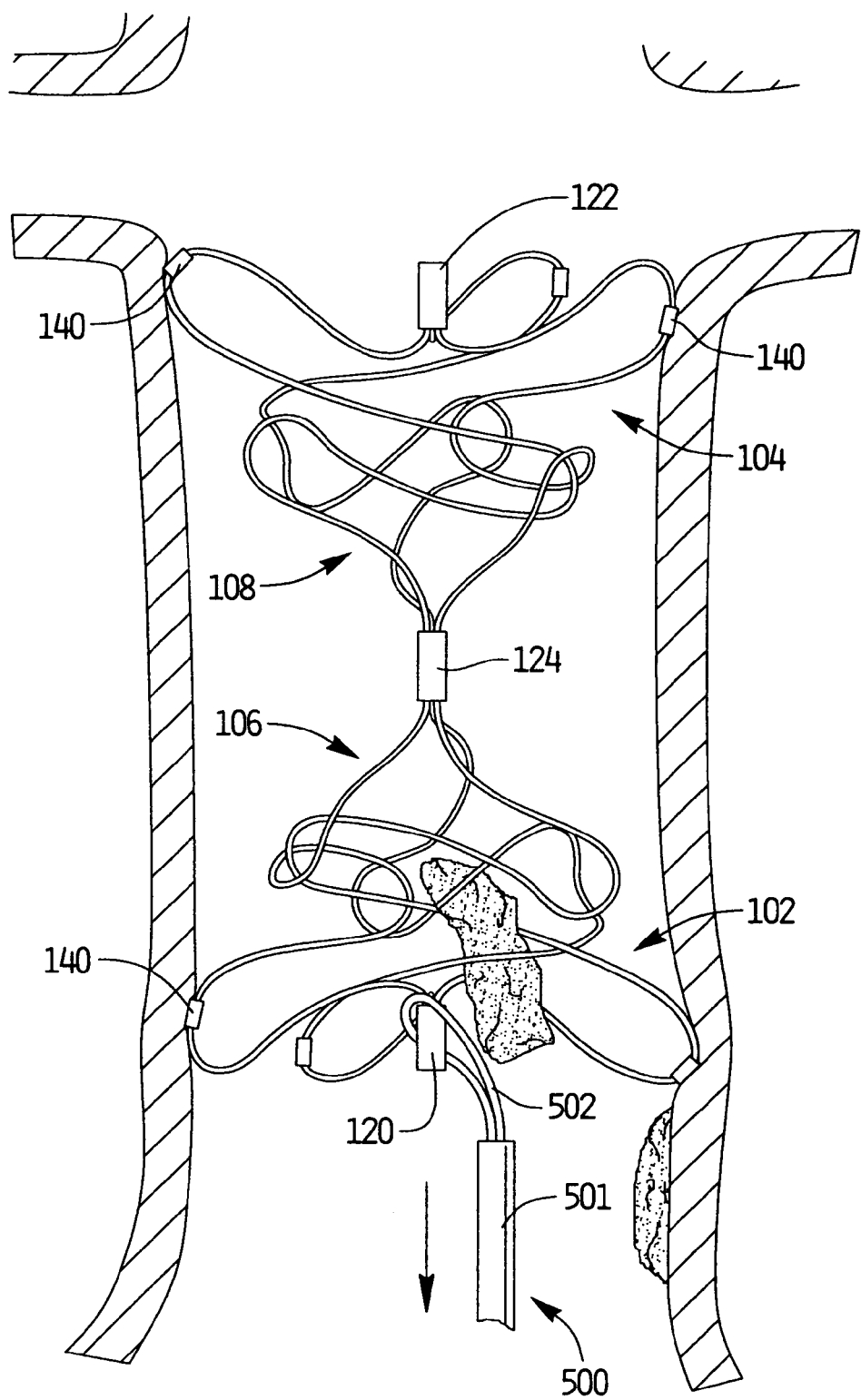
FIG_32

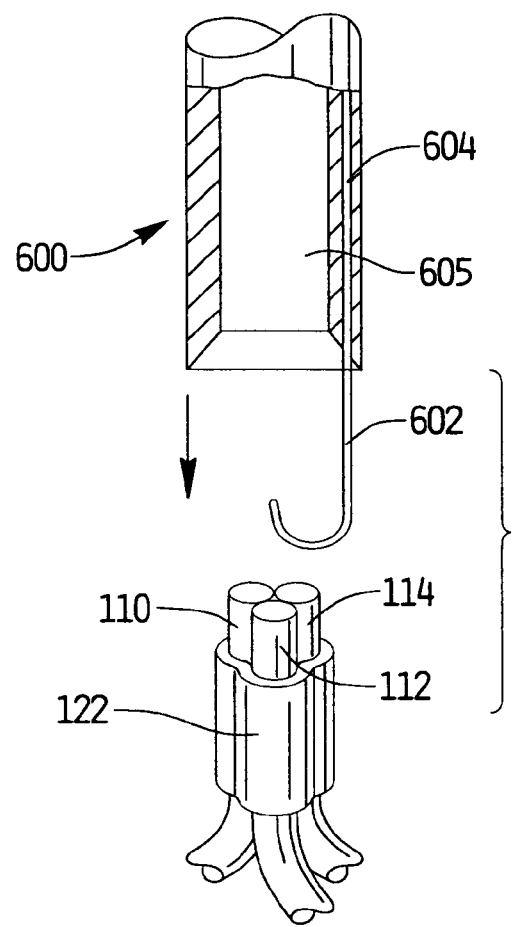
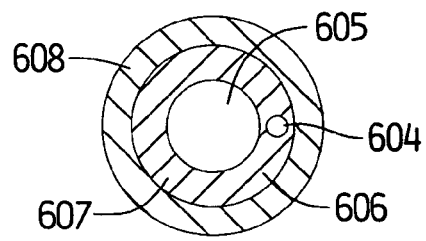
FIG_33A
FIG_33B

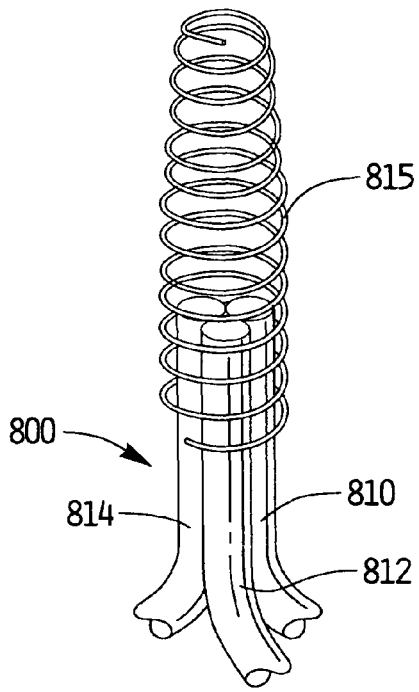
FIG_34
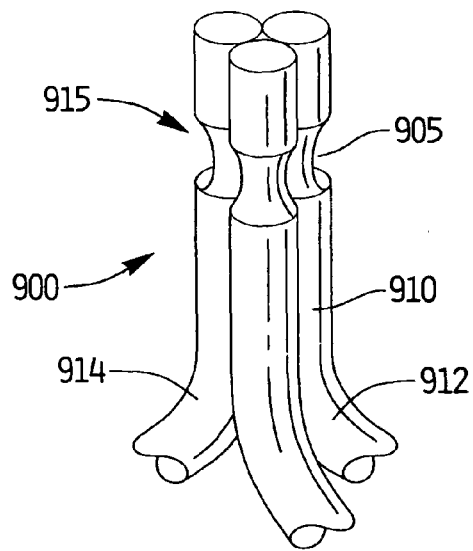
FIG_37
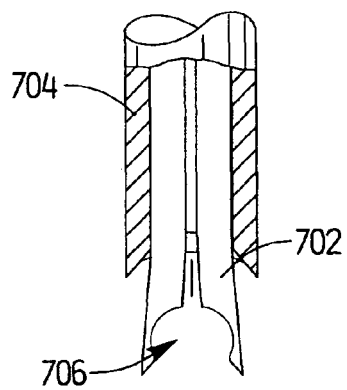
FIG_36A
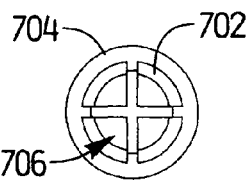
FIG_36B
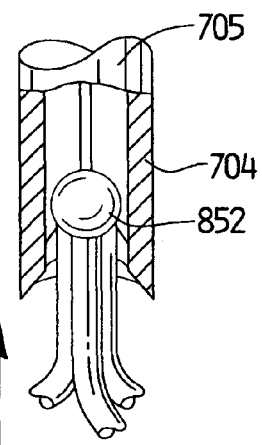
FIG_36C
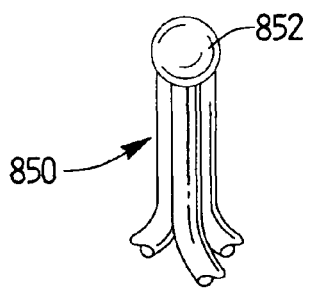
FIG_35

REMOVABLE VEIN FILTER

This application is a divisional of application Ser. No. 09/911,097, filed Jul. 23, 2001, now U.S. Pat. No. 6,783,538, which is a continuation-in-part of application Ser. No. 09/883,819, filed Jun. 18, 2001, now U.S. Pat. No. 6,623,506, and a continuation-in-part of application Ser. No. 09/883,818, filed Jun. 18, 2001, now U.S. Pat. No. 6,793,665, the entire contents of each of these applications are incorporated herein by reference.

BACKGROUND

1. Technical Field

This application relates to a vascular filter and more particularly to a vein filter for capturing blood clots within the vessel.

2. Background of Related Art

Passage of blood clots to the lungs is known as pulmonary embolism. These clots typically originate in the veins of the lower limbs and can migrate through the vascular system to the lungs where they can obstruct blood flow and therefore interfere with oxygenation of the blood. Pulmonary embolisms can also cause shock and even death.

In some instances, blood thinning medication, e.g. anticoagulants such as Heparin, or sodium warfarin can be given to the patient. These medications, however, have limited use since they may not be able to be administered to patients after surgery or stroke or given to patients with high risk of internal bleeding. Also, this medication approach is not always effective in preventing recurring blood clots.

Therefore, surgical methods to reduce the likelihood of such pulmonary embolisms by actually blocking the blood clot from reaching the lungs have been developed. One surgical method of treatment involved major surgery where the size of the vessel lumen was restricted by placement of ligatures or clips around the vein, e.g. the inferior vena cava which transports blood from the lower portion of the body to the heart and lungs. This prevented passage of dangerously large blood clots through the vein to the lungs. However, this approach is an invasive surgical procedure, requiring an abdominal incision and general anesthesia and frequently causing vessel thrombosis and lower extremity swelling. Also, there is a lengthy patient recovery time and additional hospital and surgeon expenses associated with this major surgery. In fact, oftentimes, the patients requiring the surgery are unhealthy and the major surgery and general anesthesia poses a risk in and of itself.

To avoid such invasive surgery, less invasive surgical techniques have been developed. These involve the placement of a mechanical barrier in the inferior vena cava. These barriers are in the form of filters and are typically inserted through either the femoral vein in the patient's leg or the right jugular vein in the patient's neck or arm under local anesthesia. The filters are then advanced intravascularly to the inferior vena cava where they are expanded to block migration of the blood clots from the lower portion of the body to the heart and lungs.

These prior filters take various forms. One type of filter is composed of coiled wires such as disclosed in U.S. Pat. Nos. 5,893,869 and 6,059,825. Another type of filter consists of legs with free ends having anchors for embedding in the vessel wall to hold the filter. These filters are disclosed, for example, in U.S. Pat. Nos. 4,688,553, 4,781,173, 4,832,055, and 5,059,205, 5,984,947 and 6,007,558.

Several factors have to be considered in designing vein filters. One factor is that the filter needs to be securely anchored to the internal vessel wall, while avoiding traumatic engagement and damage to the wall as well as damage to the neighboring abdominal aorta. Another factor is that the filter must be collapsible to a sufficiently small size to be easily maneuvered and atraumatically advanced intravascularly to the inferior vena cava or other target vessel. Thirdly, the filter should direct the blood clots to the center of the vessel to improve dissolution of the clot within the vessel by the blood flow.

It would be advantageous to provide a vein filter that satisfies the foregoing parameters. Namely, such vein filter would advantageously have sufficient anchoring force to retain the filter within the vessel while providing atraumatic contact with the vessel wall, would have a minimized insertion (collapsed) profile to facilitate delivery through the vascular system to the surgical site, and would enable migration of the captured blood clots to the center of the vessel. Moreover, it would also be advantageous to provide a filter that could simplify insertion through the femoral or the right jugular vein into the inferior vena cava.

Additionally, the need for a vein filter in many patients is temporary. In these instances it would be advantageous to provide a vein filter that satisfies the foregoing factors and in addition could be readily removed from the patient. It would further be advantageous if the filter could be removed minimally invasively, e.g. intravascularly, and further advantageous if the filter could be removed from the inferior vena cava in either direction, e.g. through femoral access or internal jugular vein access.

SUMMARY

The present invention overcomes the disadvantages and deficiencies of the prior art by providing a removable vessel filter comprising first and second filtering portions and first and second anchoring portions. A transverse dimension of the first filtering portion in an expanded configuration is less than a transverse dimension of the first anchoring portion in an expanded configuration, and a transverse dimension of the second filtering portion is less than a transverse dimension of the second anchoring portion. The first and second filtering portions are positioned closer to each other than the first and second anchoring portions, and the anchoring portions are formed on first and second opposite portions of the vessel filter. The vessel filter is removable from a vessel wall by engagement of either the first filtering portion or the second filtering portion.

Removal of the vessel filter by engagement with the first filtering portion removes the filter in a first direction and removal of the vessel filter by engagement with the second filtering portion removes the filter in a second different direction.

In one embodiment the filtering sections are formed by a series of wires and the filter is removable by engagement of at least one of the wires or by engagement of the series of wires by a removal instrument. In another embodiment, the filter is formed by a series of wires, a wire retaining sleeve is positioned at proximal and distal portions of the vessel filter to retain the series of wires, and the vessel filter is removable by engagement of the wire retaining sleeve by a removal instrument.

Preferably a first anchoring member extends from the first anchoring portion and a second anchoring member extends from the second anchoring portion, each of the anchoring members having a first edge to engage the vessel wall and temporarily retain the vessel filter within the vessel. The anchoring member also preferably includes a second sharpened edge opposite the first sharpened edge to engage the vessel wall. The sharp edges engage the vessel wall and temporarily retain the vessel filter within the vessel as the anchoring members are disengagable from the vessel wall to remove the filter as application of an axial force to the filter in the first direction or in the second direction collapses the filter.

Preferably, in the expanded configuration, the transverse dimensions of the first and second anchoring portions are substantially equal and the transverse dimensions of the first and second filtering portions are substantially equal, forming a symmetrical filter for insertion in a first or second direction and removal in the first or second direction. Preferably, each of the filtering portions progressively increases in diameter towards its respective anchoring portion.

The present invention also provides a removable vessel filter comprising a first portion, a second portion and an intermediate portion between the first and second portions. The first portion increases in diameter from the intermediate portion towards a first end and the second portion increases in diameter from the intermediate portion towards a second end. A region closer to the intermediate portion forms a filter portion and the vessel filter has at least one vessel engaging member to temporarily retain the filter within the vessel and allow subsequent disengagement from the vessel wall and removal of the filter.

The filter is preferably formed by at least one wire, wherein the at least one wire forms a part of the first, second and intermediate portions. The at least one wire can be enagaged by a filter removal tool to remove the filter. The filter may further comprise a retaining sleeve at the proximal and distal portions to retain the at least one wire, wherein either of the retaining sleeves are engagable by a removal tool to remove the filter.

The present invention also provides a removable vessel filter comprising a proximal portion forming an anchoring portion, a distal portion forming a filtering portion, a first wire section extending from the proximal portion to the distal portion and forming a series of loops extending substantially in a first direction, a second wire section extending from the proximal to the distal portion and forming a series of loops extending substantially in a second direction different than the first direction, and at least one anchoring member configured to engage the vessel wall and temporarily retain the filter within the vessel. The vessel filter is composed of shape memory material, is movable from a collapsed configuration for delivery to the vessel to an expanded configuration for engagement with the vessel, and is further movable towards the collapsed configuration upon application of an axial force thereto to enable removal of the vessel filter from the vessel.

The anchoring member preferably comprises a tubular member positioned on at least one of the wire sections and has a first sharp end for contacting the vessel wall to temporarily retain the filter. The plurality of wire sections of the vessel filter may be formed by at least first and second separate wires, and the filter is removable by engagement of the at least two wires by a removal tool. The filter can alternatively be removed by engagement of a wire retaining sleeve.

A method of implanting and subsequently removing a vein filter in the inferior vena cava of a patient is also provided comprising:
  inserting through a vessel in either a first direction or a second direction a catheter having a filter positioned therein in a collapsed configuration so that wire sections of the filter are in a substantially elongated configuration;
  releasing the filter from the catheter to enable the filter to move to an expanded configuration, in the expanded configuration a pair of mounting portions expand to a first diameter and a pair of filter portions expand to a second smaller diameter;
  leaving the filter in the vessel for a period of time;
  inserting after the period of time in either the first direction or the second direction a filter removal tool to engage at least one of the wire sections; and
  moving the tool in a direction opposite the insertion direction of the tool to move the filter towards the collapsed configuration.

In one embodiment, the filter removal tool has at least one movable jaw and the method further comprises the step of actuating the at least one jaw to clamp one of the wire sections. In another embodiment, the wire sections comprise first, second and third wires, the filter removal tool has first, second and third pairs of jaws, and the method further comprises actuating at least one of the jaws of each pair of jaws to clamp each of the first, second and third wires. In another embodiment, the step of inserting a removal tool to engage at least one of the wire sections includes manipulating the filter removal tool so a hook on the tool grasps at least one of the wire sections. The step of manipulating the filter removal tool can include manipulating first, second and third hooks of the tool so that each hook engages one of the first, second and third wires.

In alternate embodiments, the step of inserting the tool to engage at least one of the wire sections comprises the step of engaging at least one of the wire sections with locking barbs of the removal tool or engaging at least one of the wire sections with a collapsible braid of the removal tool to frictionally engage at least one of the wire sections. In another embodiment, the filter terminates in an atraumatic tip and the step of inserting the tool to engage at least one of the wire sections comprises the step of engaging the atraumatic tip.

The present invention also provides a method of implanting and subsequently removing a vein filter in the patient's inferior vena cava comprising:
  inserting through a vessel a catheter having a filter positioned therein in a collapsed configuration so that wire sections of the filter are in a substantially elongated configuration, the wire sections held at a proximal portion by a proximal retaining sleeve and held at a distal portion by a distal retaining sleeve;
  releasing the filter from the catheter to enable the filter to move to an expanded configuration, in the expanded configuration a pair of mounting portions expand to a first diameter and a pair of filter portions expand to a second smaller diameter;
  leaving the filter in the vessel for a period of time;
  inserting a filter removal tool in a first direction after a period of time to engage one of the retaining sleeves; and
  moving the tool in a direction opposite the first insertion direction of the tool to move the filter towards the collapsed configuration.

In one embodiment, the filter removal tool comprises a snare, and the method of inserting the tool to engage the retaining sleeve further comprises the step of tightening the snare against the retaining sleeve of the filter. In another embodiment, the filter removal tool comprises a grasper having at least one movable jaw, and the method of inserting the tool to engage the retaining sleeve further comprises the step of actuating the at least one movable jaw to clamp the jaw on the retaining sleeve.

In any of the foregoing methods the filter can be inserted through the internal jugular vein, superior vena cava or through the femoral vein and removed through the internal jugular vein, superior vena cava or the femoral vein. Preferably the methods further comprise the step of delivering cold saline into the catheter to maintain the filter in the collapsed configuration. Preferably, the step of releasing the filter comprises withdrawing the catheter to expose the filter.

BRIEF DESCRIPTION OF THE DRAWINGS

Preferred embodiment(s) of the present disclosure are described herein with reference to the drawings wherein:

FIG. 1 is a perspective view of a first embodiment of the vein filter of the present invention shown in the expanded configuration;

FIG. 2 is a side view of the vein filter of FIG. 1;

FIG. 3 is a top view of the vein filter of FIG. 1;

FIG. 4 is a front view of the vein filter of FIG. 1;

FIG. 5A is a perspective view of the vein filter of FIG. 1 in the collapsed configuration for delivery through a catheter or sheath into the vessel;

FIG. 5B is an enlarged view of a portion of the filter in the collapsed configuration of FIG. 5A showing the intermediate and proximal crimping sleeves;

FIG. 5C is an enlarged side view of the portion of the filter shown in FIG. 5B;

FIG. 6A is a transverse cross-sectional view of the vein filter of FIG. 1 in the collapsed configuration of FIG. 5 showing an anchor member and adjacent wire within the delivery sheath;

FIG. 6B is a transverse cross-sectional view of the vein filter of FIG. 1 in the collapsed configuration of FIG. 5, showing a crimping sleeve encircling two wires within the delivery sheath;

FIG. 7 is perspective view of a second embodiment of the vein filter of the present invention formed of a single wire and shown in the expanded configuration;

FIG. 8 is a perspective view of a third embodiment of the vein filter of the present invention formed of a single wire with a central (intermediate) crimping sleeve, and shown in the expanded configuration;

FIG. 9 is a perspective view of another alternate embodiment of the vein filter of the present invention having two filtering portions and two anchoring portions shown in the expanded configuration;

FIG. 10A is side view of the vein filter of FIG. 9 in the expanded configuration;

FIG. 10B is a side view similar to FIG. 10A except at a slightly different angle;

FIG. 11 is a front view of the vein filter of FIG. 9 in the expanded configuration;

FIG. 12A is a perspective view of the vein filter of FIG. 9 in the collapsed configuration for delivery through a catheter or sheath into the vessel;

FIG. 12B is an enlarged side view of the distal and middle portions of the vein filter of FIG. 9 in the collapsed configuration of FIG. 12A;

FIG. 12C is an enlarged perspective view of a portion of the vein filter of FIG. 12A showing the axial displacement of the anchoring members;

FIG. 12D is a view similar to FIG. 12A except showing the alternate embodiment of the vein filter of FIG. 10C having a series of anchoring members on each of the wires at the proximal and distal portions;

FIG. 12E is a side view of the middle and distal portions of the filter of FIG. 12D;

FIG. 13A is a transverse cross-sectional view of the vein filter of FIG. 9 in the collapsed configuration of FIG. 12 showing the crimping sleeve encircling three wires within the delivery sheath;

FIG. 13B is a transverse cross-sectional view of the vein filter of FIG. 9 in the collapsed configuration of FIG. 12 showing an anchor member and adjacent wires within the delivery sheath;

FIGS. 14-17 illustrate the steps of insertion of the vein filter of FIG. 9 within the inferior vena cava of a patient in accordance with a first method, wherein:

FIG. 14 illustrates insertion of the delivery catheter through the femoral vein;

FIG. 15 illustrates the delivery sheath being advanced to the inferior vena cava just below (upstream) the juncture of the renal arteries;

FIG. 16 illustrates the delivery sheath being withdrawn to enable one of the anchoring portions and one of the filtering portions to move to the expanded configuration; and FIG. 17 illustrates the delivery sheath fully withdrawn to expose the other filtering portion and the other anchoring portion to enable movement to the expanded configuration;

FIG. 18A is an enlarged view of the expanded filter of FIG. 17 showing a blood clot captured in the filter;

FIG. 18B is an enlarged view of an alternate embodiment of the filter in the expanded condition having longitudinally offset crimping sleeves;

FIG. 19 is an enlarged view of one embodiment of the anchoring tube of the present invention having ground edges engaging the vessel wall;

FIG. 20 is an enlarged view of an alternate embodiment of an anchoring tube of the present invention having beveled edges engaging the vessel wall;

FIGS. 21-23 illustrate insertion of the vein filter of FIG. 9 within the inferior vena cava in accordance with a second method, wherein:

FIG. 21 illustrates insertion of the delivery catheter through the right jugular vein;

FIG. 22 illustrates the delivery sheath being advanced downwardly past the juncture of the renal arteries to the inferior vena cava; and FIG. 23 illustrates the delivery sheath being withdrawn to enable one of the anchoring portions and filtering portions to move to the expanded configuration;

FIG. 24 illustrates insertion of the vein filter of FIG. 9 into the superior vena cava in accordance with a third method of the present invention;

FIG. 25 is a side view, with the vessel shown in cross-section, illustrating a first embodiment of an instrument for grasping the filter wires for removing the vein filter of FIG. 9 through the internal jugular vein;

FIG. 26A is a side view of a distal end of a second embodiment of an instrument, having a series of barbs, for grasping the filter wires for removing the vein filter through the internal jugular vein;

FIG. 26B is a side view of the instrument of FIG. 26A illustrating the welded wire end of the vein filter of FIG. 26A retained within the instrument;

FIG. 27A a side view of a distal end of a third embodiment of an instrument, having a collapsible braided structure, for grasping the filter wires for removing the vein filter of FIG. 26A through the internal jugular vein;

FIG. 27B is a side view of the instrument of FIG. 27A illustrating the welded end of the vein filter retained within the instrument;

FIG. 28 a side view of a distal end of a fourth embodiment of an instrument, having a hook, for grasping the filter wires for removing the vein filter of FIG. 26A through the internal jugular vein;

FIG. 29 a side view of a distal end of a fifth embodiment of an instrument, having a spring biased finger, for grasping the filter wires for removing the vein filter of FIG. 26A through the internal jugular vein;

FIG. 30 is a side view, with the vessel shown in cross-section, illustrating a first embodiment of an instrument for grasping the crimping sleeve for removing the vein filter of FIG. 9 through the internal jugular vein;

FIG. 31 is a side view, with the vessel shown in cross-section, illustrating a second embodiment of an instrument for grasping the crimping sleeve for removing the vein filter of FIG. 9 through the internal jugular vein;

FIG. 32 is a side view illustrating the instrument of FIG. 31 used for removing the vein filter through the femoral vein;

FIG. 33A is a side view of a distal end of a third embodiment of an instrument, having a hook, for grasping the crimping sleeve for removing the vein filter through the internal jugular vein;

FIG. 33B is a transverse cross-sectional view of the instrument of FIG. 33A;

FIG. 34 illustrates a distal end of an alternate embodiment of the vein filter terminating in an atraumatic spring tip;

FIG. 35 illustrates a distal end of another alternate embodiment of the vein filter terminating in an atraumatic ball tip;

FIG. 36A is a side view of a distal end of a first embodiment of an instrument, having a collet, for grasping the ball tip of the vein filter of FIG. 35 for removing the vein filter through the internal jugular vein;

FIG. 36B is a front view of the instrument of FIG. 36A;

FIG. 36C is a side view showing the ball tip retained within the removal instrument of FIG. 36A; and FIG. 37 illustrates a distal end of yet another alternate embodiment of the vein filter having a recess slightly proximal of the distal end.

DETAILED DESCRIPTION OF PREFERRED EMBODIMENTS

Figure 10C:
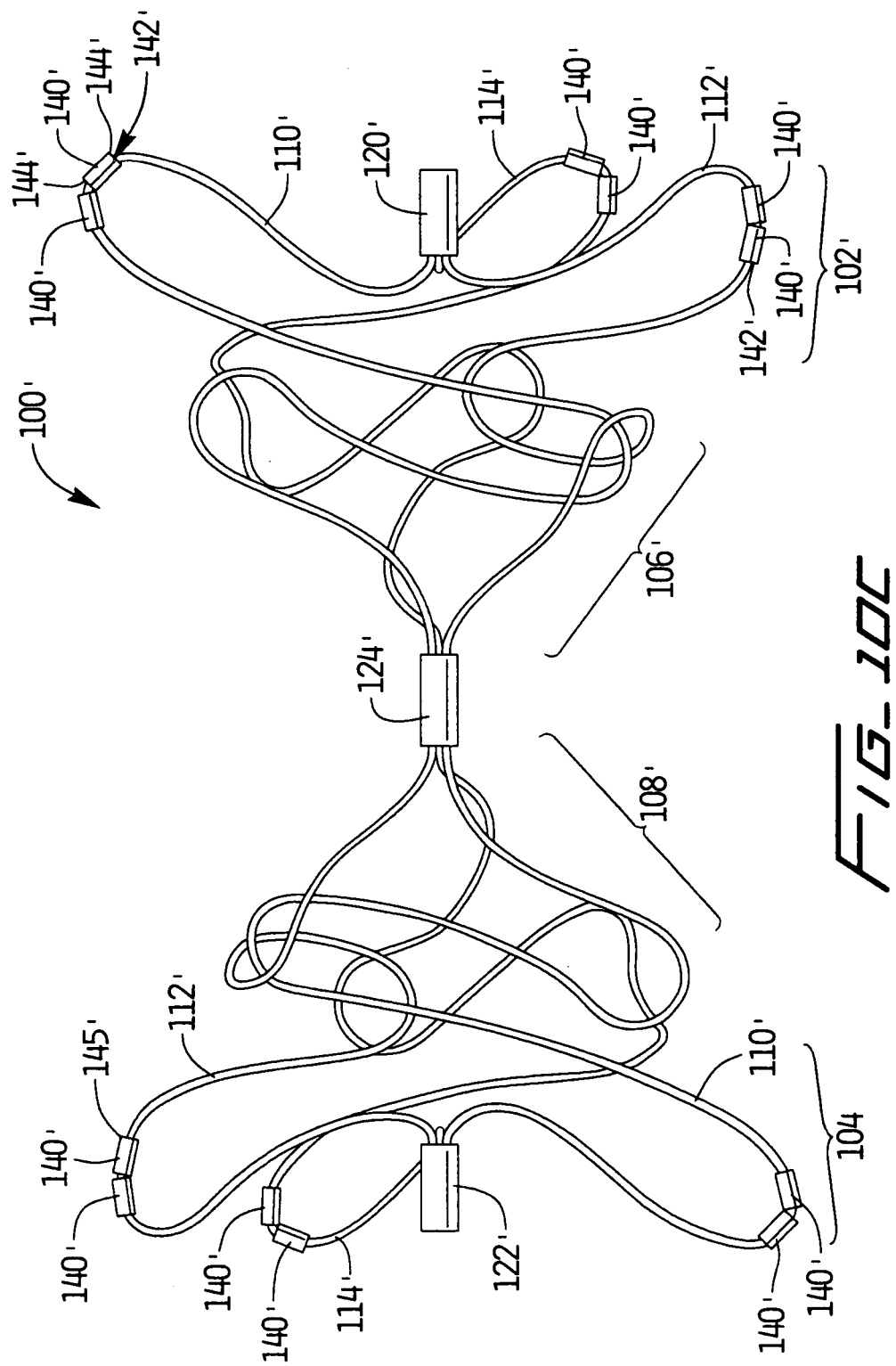
FIG. 10C is a view similar to FIG. 10A except showing an alternate embodiment of the filter of the present invention in the expanded configuration having multiple anchoring members on each of the wires.

Turning now to the drawings, wherein like reference numerals identify similar or like components throughout the several views, several embodiments of vein filters of the present invention are described for placement within the inferior vena cava to capture blood clots or other particles which could otherwise pass to the lungs. These filters are movable from a low profile collapsed configuration to facilitate insertion through the delivery sheath to an expanded position to enable the anchoring members to atraumatically contact the vessel walls to secure (mount) the filter within the inferior vena cava. The anchoring members are configured to securely retain the filter in the vessel while allowing for disengagement from the vessel wall, if desired, to enable removal of the filter. The wire(s) which form the vein filters of the present invention are looped to form an anchoring portion and a narrowed filtering portion, as will be described in detail below.

With reference first to the embodiment of FIGS. 1-6, and turning initially to FIG. 1, this first embodiment of the vein filter of the present invention is designated generally by reference numeral 10. Vein filter 10 is formed by a pair of wires, designated by reference numerals 12 and 14. Wires 12 and 14 are preferably circular in cross-section having a diameter preferably ranging from about 0.011 inches to about 0.020 inches, and preferably about 0.012 inches. The wires 12 and 14 are held together, side by side, at their distal ends by a distal crimping sleeve 20 and held together, side by side, at their proximal ends by a proximal crimping sleeve 22. To provide additional support and overall rigidity to the filter 10, a central or intermediate crimping sleeve 24 is provided at an intermediate portion of wires 12 and 14 to retain middle portions of the wire together in a side-by-side relationship.

Although preferably held side by side by crimping sleeves, the wires can also be held by other means such as being welded or glued. An example of the wire ends being welded together is illustrated in FIGS. 26A and 27A.

As can be appreciated from FIGS. 1-2, the wires 12 and 14 are wound in identical manners, except opposite to one another. That is, wire 12, starting from proximal crimping sleeve 224, weaves back and forth across an imaginary centerline "C" (or central longitudinal axis) to form a series of loops 12b, 12d, 12g, 12i and 12k, on one side of the centerline. Bends or curves 12a, 12c, 12e, 12f, 12h, 12j and 12l are on the other side of the centerline and form transitions for formation of the loops in wire 12. Each of the bends 12a, 12c, 12e, 12f, 12h, 12j and 12l faces in the downward direction enabling each of the loops 12b, 12d, 12g, 12i and 12k to open in an upward direction as oriented in FIGS. 1 and 2.

Wire 14 also weaves back and forth across the centerline forming loops 14b, 14d, 14g, 14i and 14k on one side of the centerline and curves and bends 14a, 14c, 14e, 14f, 14h, 14j and 14l on the other side of the centerline to from transitions for the loops. Each of the bends 14a, 14c, 14e, 14f, 14h, 14j and 14l faces in the upward direction and each of the loops 14b, 14d, 14g, 14i and 14k opens in the downward direction as oriented in FIGS. 1 and 2. Thus, viewed another way, wire 12 forms upwardly directed loops (as viewed in the orientation of FIGS. 1 and 2) and wire 14 forms downwardly directed loops with the wire loops and bends 12a-12l approximately 180 degrees out of phase with the corresponding wire loops and bends 14a-14l.

A central portion 12m, 14m of wires 12 and 14, respectively, forms partial loops and extends substantially linearly through the central crimping sleeve 24 where they are contiguous and aligned side by side. The wires 12 and 14 are preferably also contiguous as they extend linearly through the proximal, and distal crimping sleeves 22, 20, respectively. Partial loops 12n and 14n are formed in wires 12 and 14 before extending through distal crimping sleeve 20 and partial loops 12p, 14p extend from proximal crimping sleeve 22. In the other regions, the wires preferably do not touch as the loops are spaced apart and the loops of wire 12 do not cross over the loops of wire 14.

The center of the radii of the loops on one side as viewed in FIG. 1, i.e. loops 14i, 12g, 14d, and 12b, are preferably substantially aligned such that an imaginary line drawn through such centers would be substantially parallel to the longitudinal axis of the filter 10. The center of the radii of the loops 14k, 12i, 12d and 14b on the other side of the filter 10 are also preferably substantially aligned such that an imaginary line drawn through such centers would be substantially parallel to the longitudinal axis of the filter 10. The two imaginary lines lie in substantially the same transverse plane.

The wires 12, 14 of filter 10 form an anchoring or mounting portion 30 and a filtering portion 28. The anchoring portion 30 is formed at a proximal portion to engage the vessel wall for securement of the filter 10. The filtering portion 28 is formed at a distal portion and has a diameter less than the diameter D1 (FIG. 3) of the anchoring portion 30. The diameter of the filtering portion is sufficiently small to capture blood clots and prevent its passage through the filter 10.

It should be appreciated that the terms proximal and distal are utilized for convenience for orientation purposes, since if the filter 10 is inserted into the inferior vena cava through the internal jugular vein instead of the femoral vein, the portion closer to the user, e.g. the "proximal portion", will instead be the filtering portion 28.

In the illustrated embodiment, the anchoring portion 30, which includes the region between the intermediate and proximal crimping sleeves 24, 22, is substantially uniform in diameter (D1) or height. The filter portion 20, which includes the region between the intermediate sleeve 24 and the distal crimping sleeve 20, progressively decreases in diameter towards the distal sleeve 20 from diameter D2 to diameter D3. Consequently diameter D2 of filter portion 32 is greater than diameter D3 of filter portion 20. This decrease in diameter helps to cause migration of the blood clots towards the center of the filter 10 to facilitate dissolution by the blood flow. Thus, the region between the drawn diameters D2 and D3 functions as the filtering portion. As noted below, it should be appreciated that the anchoring and filtering regions are not rigidly defined and the diameters D2 and D3 and the portions 30 and 28 are identified for convenience.

Preferably, the diameter D1 of the anchoring portion 30 ranges from about 18 mm to about 30 mm. The diameter D2 of the filtering portion 28 preferably ranges from about 17 mm to about 29 mm; and the smaller diameter D3 of the filtering portion 28 preferably decreases to as small as about 0.5 mm at the distal sleeve 20. Other dimensions are contemplated.

It should be understood that the anchoring portion 30 defined herein defines a region of the filter which is utilized to retain (mount) the filter 10 inside the vessel and the filtering portion 28 defines the region which captures particles such as blood clots. Consequently the region of the anchoring portion can alternatively terminate more distally of the intermediate crimping sleeve 24 or terminate more proximally of the crimping sleeve 24. Similarly, a region of the filtering portion, i.e. the progressive decrease in diameter, can alternatively begin proximally of the intermediate crimping sleeve 22 or begin further distally than as illustrated in FIGS. 1 and 2. These alternatives are viable so long as a sufficient region is provided for anchoring the filter and a sufficient narrowed filtering region is provided to capture blood clots or other particles. Thus, it should be appreciated that the anchoring and filtering portions 30, 28 need not be defined by the regions separated by intermediate crimping sleeve 24.

The anchoring portion 30 of the filter 10 includes at least one vessel wall retention or securement (anchoring) member, designated by reference numeral 40. The retention member 40 is preferably in the form of a stainless steel tube and has a lumen 42 to receive respective wires 12 and 14. The anchoring tube 40 (or 50) is preferably attached to the wire 12 or 14 by crimping or welding. The anchoring tube 40 has opposed beveled edges 44, 46 which frictionally engage portions of the vessel wall in the manner described below. Alternatively, the anchor member can be in the form of a cylindrically shaped tube 50 (see FIG. 5) with the edges 52 sharpened, e.g. by grinding, to engage the vessel. This is also described in more detail below. Surface 45 abuts the vessel wall to provide a large area of contact (see e.g. FIGS. 19 and 20). This configuration of the anchoring member, which engages the vessel wall at its opposite ends, provides secure retention of the filter to prevent migration. This configuration also allows the anchoring members to be readily disengaged from the vessel wall as the filter is collapsed to enable removal from the vessel if desired.

In the preferred embodiment, one tube 40 (or 50) is positioned on wire 12, at the largest diameter region of the anchoring portion 30, tangent with loop 12d; and another tube 40 (or 50) is positioned on wire 14, also at the largest diameter region of the anchoring portion 30, tangent with loop 14d. Thus, the anchoring members 40 (or 50) are approximately 180 degrees apart. In this manner, when the filter 10 moves to its expanded configuration, the anchoring tubes will engage opposing sides of the vessel wall as described below. Although two anchoring members are shown, additional anchoring members can be provided. This is described below in conjunction with FIGS. 12D and 12E, it being understood that the train of staggered anchoring members could be provided in this embodiment of the filter as well.

The collapsed configuration of the filter 10 for delivery inside the vessel will now be described with reference to FIGS. 5A-5C and 6A-6B. Note that although the collapsed configuration is illustrated with cylindrical tubes 50, it is understood that anchoring tubes 40 would be positioned in a similar manner.

When collapsed, the first and second wires 12, 14 are in a straightened configuration substantially parallel with one another and substantially aligned with their respective longitudinal axis. The cylindrical anchoring members 50 are axially displaced to conserve space within the delivery catheter. Consequently, as shown in the transverse sections of FIGS. 6A and 6B, the largest cross sectional area occupied by the filter 10 is defined by the outer diameter D4 of one of the wires (e.g. wire 14) plus the outer diameter D5 of the anchoring tube 50. Since the other anchoring tube(s) are staggered, i.e. axially displaced, in the collapsed configuration, the overall collapsed diameter is minimized which would not be the case if the anchoring tubes 50 were axially aligned in the collapsed configuration since the diameter would be then be defined by the sum of the diameters D5 of adjacent anchoring tubes. (2×D5). This axial displacement of the anchoring tube thereby enables the size (diameter) of the delivery sheath 210 to be minimized. A slight gap, not shown, could be provided between the outer wall of the anchoring tube 50 and delivery sheath 210 to provide clearance to facilitate exit from the sheath 210.

FIG. 6B shows the diameter of the two wires within the crimping sleeve 22, with the total cross sectional region occupied by the collapsed filter defined by the outer diameter D6 of the sleeve 22. A slight gap between the outer diameter of the crimping sleeve 22 and delivery sheath 210 is designated by reference letter "g".

Stated another way, the inner diameter of the crimping sleeve is equal to the sum of the outer diameters of the wires 12, 14, with the thickness "t" of the sleeve defined by the distance between the inner wall and outer wall and being sufficient to rigidly retain the wires. For this given diameter, the anchoring tube is preferably maintained equal to or less than the numerical difference between the outer diameter of the sleeve and the outer diameter of the wire. This keeps the overall cross-sectional region (or height) of the filter in the collapsed position at a minimum as other portions of the filter 10 in the collapsed position will not exceed the outer diameter of the crimping sleeve.

As noted above, the outer diameter D4 of the wires 12 and 14 is preferably about 0.012 inches. The inner diameter D6 of each crimping sleeve preferably ranges from about 0.022 inches to about 0.040 inches, and preferably is about 0.024 inches. That is, the inner diameter of the crimping sleeve is preferably twice the diameter of the wire. The outer diameter of each crimping sleeve preferably ranges from about 0.050 inches (18 gauge) to about 0.065 inches (16 gauge), and is preferably about 0.058 inches (17 gauge). The outer diameter D5 of the anchoring tube preferably ranges from about 0.030 inches to about 0.054 inches, and is preferably about 0.046 inches. With these dimensions, a 6 French delivery sheath 27 (2 mm in outer diameter) to deliver the filter 10 can be utilized.

To enable movement between an expanded and collapsed configuration, wires 12 and 14 are preferably made of shape memory metal material, such as Nitinol, a nickel titanium alloy. The memorized configuration of the filter 10 is shown in FIG. 1. To facilitate passage of the wires 12 and 14 through the lumen of the delivery sheath 210 and into the vessel, cold saline is injected into the delivery sheath 210 and around the wires 12 and 14 in their collapsed position within the delivery sheath 210. This shape memory material characteristically exhibits rigidity in the austenitic state and more flexibility in the martensitic state. The cold saline maintains the temperature dependent wires 12, 14 in a relatively softer condition as they are in the martensitic state within the sheath. This facilitates the exit of wires 12 and 14 from the sheath 210 as frictional contact between the wires 12, 14 and the inner surface of the sheath would otherwise occur if the wires were maintained in a rigid, i.e. austenitic, condition.

Once ejected from the delivery sheath 210, the wires are no longer cooled and are exposed to the warmer body temperature, which causes the wires to return their austenitic memorized configuration of FIG. 1.

The filter 10 can be inserted through the jugular vein in the neck of the patient or through the femoral vein in the leg of the patient. It can also be inserted through the superior vena cava. If inserted through the femoral vein, the filter would be positioned within sheath 21 so that the anchoring portion 30 is closer to the user and the filtering portion 28 is further from the user. If inserted through the jugular or superior vena cava, the filter would be positioned within sheath 21 so that the anchoring portion 30 is further from the user and the filtering portion 28 is closer to the user. Insertion of the filter will be better understood from the detailed description below of the filter insertion methods.

As noted above, due to the engagement of the vessel wall by the anchoring tubes 50, and the configuration of the vein filter 10, the filter can be readily removed from the inferior vena cava. Instruments such as those described below in connection with FIGS. 25-33 can be inserted through the internal jugular vein (or the superior vena cava) and advanced into the inferior vena cava to grasp the filter in the manner described below for filter 100. That is, a removal tool can be utilized to grasp one or both of the wires of the filter, or alternatively, used to grasp the proximal crimping sleeve 22 to collapse the filter and disengage the anchoring members from the vessel wall. The filter could then be removed through the femoral vein.

FIG. 8 illustrates an alternate embodiment of the filter of the present invention, designated generally by reference numeral 60. Filter 60 is similar to filter 10, except instead of being formed of two wires, filter 60 is formed of a single wire 61. Filter 60 is crimped at the proximal end by sleeve 72 and at a middle or intermediate portion by crimping sleeve 74. The distal end 66 of filter wire 60 loops around at loop 68, and is therefore not crimped with a sleeve as in the embodiment of FIG. 1. Filter 60 also preferably has anchoring tubes (not shown) on anchoring portion 62 similar to anchoring tubes 40 of FIG. 1 or tube 50 of FIG. 5 on loops 67 and 69. In all other respects, e.g. narrowed filtering portion 64, loops about 180 degrees out of phase, etc., filter 60 is identical to filter 10.

FIG. 7 illustrates another alternate embodiment of the filter of the present invention formed by a single wire. Wire 82 of filter 80 wraps in a similar fashion as wire 61 of filter 60. That is, wire 82 forms alternating loops, i.e. downwardly directed and upwardly directed, as oriented in FIG. 7, as it extends from a proximal end 85 in anchoring portion 86 to distal loop 87 at a filtering portion 88. Wire 82 then extends proximally from the distal loop 87 in an alternating loop pattern forming upwardly and downwardly directed loops. Filter 80 preferably includes a proximal crimping sleeve (removed to illustrate the wire) to retain the free ends 87, 89 of wire 82. Filter 80 also preferably includes an anchoring tube (not shown) on respective loops of the anchoring portion 86, similar to anchor 40 of FIG. 1 or anchor 50 of FIG. 5.

In the embodiments of FIGS. 7 and 8, the wire loops at the distal end and the wire ends are crimped, welded or secured by other means at the proximal end. It is also contemplated that alternatively the wire can loop at its proximal end and the two ends secured at the distal end. Also, instead of a crimping sleeve, the wire ends can be glued, welded (see e.g. FIGS. 26A and 27A) or attached by other means.

Filters 60 and 70 can be removed through the femoral vein in a similar manner as filter 10.

An alternate embodiment of the filter of the present invention, having two anchoring portions and two filtering portions is illustrated in FIGS. 9-13 and designated generally by reference numeral 100. The filter 100, having two symmetric anchoring and filtering portions, can be inserted into the inferior vena cava in either direction, e.g. downwardly from the right jugular vein access or upwardly from the femoral vein access, without concern of its proximal/distal orientation. The filter 100, having two symmetric portions, can also be removed in either direction, regardless of the direction which it is inserted.

With initial reference to FIGS. 9 and 10, filter 100 is formed by three wires 112, 114 and 116. The three wires 112, 114 and 116 form first and second anchoring portions 102, 104 and first and second filtering portions 106, 108. The first filtering and anchoring portions 102, 106 extend between proximal crimping sleeve 120 and intermediate (central) crimping sleeve 124; the second filtering portion 108 and anchoring portion 104 extend between intermediate crimping sleeve 124 and distal crimping sleeve 122. Anchoring portion 102 is substantially identical to anchoring portion 104, except it extends in the opposite direction. Similarly, the filtering portion 106 is substantially identical to filtering portion 108 except it also extends in the opposite direction. By providing two symmetrical portions, the filter can be placed inside a delivery catheter and inserted either through the jugular vein or the femoral vein using the same delivery catheter and in either proximal/distal orientation.

As mentioned above with respect to the first embodiment, although the wires are described as being held in side by side relationship by a crimping sleeve, alternatively the wires can be welded (see e.g. FIGS. 26A, 27A), glued, or held together by other means.

The provision of two anchoring portions 104, 102 on opposing ends helps to center the filter 100 within the vessel which in turn helps to maintain the captured blood clots in the center of the filter 100. If the blood clots are maintained in the center, they will more easily be dissolved or washed away by the blood flow.

The three wires 110, 112, 114 each form a series of loops which are about 120 degrees out of phase with the loops of the adjacent wires. More specifically, wire 110 forms three loops 110a, 110b, and 110c between the proximal and intermediate crimping sleeves 120, 124 with loops 110a and 110c extending in a first direction and a loop 110b extending in an opposite second direction. Wire 110 further forms two loops 110d and 110*f*, extending in the second direction and one loop 110*e* extending in the first direction in the region between the intermediate crimping sleeve 124 and the distal crimping sleeve 122.

Wire 112 in the first anchoring/filtering portion defined between the proximal and intermediate crimping sleeves 120, 124 forms two loops 112*a*, 112*c* extending in a third direction and a third loop 112*b* extending in a fourth direction opposite the third direction. In the second anchoring/filtering portion defined between the intermediate and distal crimping sleeves 124, 122, loops 112*d* and 112*f* of wire 112 extend in the fourth direction and loop 112*e* extends in the third direction.

Wire 114 in the first anchoring/filtering portion defined between the proximal and intermediate crimping sleeves, forms two loops 114*a*, 114*c* extending in a fifth direction and a third loop 114*b* extending in a sixth opposite direction. Loops 114*d* and 114*f* extend in the sixth direction and loop 114*e* extends in the fifth direction. These loops 114*d*, 114*e* and 114*f* are formed in the second anchoring/filtering portion between the distal and intermediate crimping sleeves 122, 120.

The corresponding loops of wires 110, 112, 114, e.g. loops 110*a*, 112*a*, 114*a*; loops 110*b*, 112*b*, 114*b*; etc., are preferably about 120° out of phase. It should be appreciated that arrangements other than 120 degree spacing are contemplated. Additionally, "opposite" directions of the loops is not limited to 180 degrees, but encompasses different directions. The loops of the wires have axially spaced apexes in both the mounting and filter portions.

An anchoring member 140 is positioned on each of the wires 110, 112, 114 in the first anchoring portion 102 and the second anchoring portion 104. More specifically, the anchoring members 140 are positioned on the region of the wires 110, 112 and 114 having the largest diameter (height) H or greatest distance from the longitudinal axis, namely on loops 110*a*, 112*a*, 114*a* and loops 110*f*, 112*f* and 114*f* as shown. The distances H are preferably substantially equal but alternatively can vary. Note the anchoring members are removed from FIGS. 9, 10B and 11 for clarity.

With reference to FIG. 10A, the anchoring (securement) member has a lumen 142 to receive the respective wire therethrough. The anchoring member 140 is preferably a cylindrical shaped metallic tube with opposed sharpened edges 144 formed by grinding the ends. It should be understood, that the anchoring tube 40 of FIG. 1 with sharpened bevelled edges could alternatively be utilized. The ground edges 144 are designed to frictionally engage the vessel wall in the manner described in more detail below to retain the filter 100 inside the vessel.

In the alternate embodiment of FIG. 10C, filter 100' has a pair of anchoring members 140' on each of the wires 110', 112' 114' in the first anchoring portion 102' and in the second anchoring portion 104'. In all other respects, the filter 100' is identical to filter 100 with corresponding parts labeled with a prime ('). It is also contemplated that additional anchoring members can be placed on the wires 110', 112' and 114'.

The diameter or height of the anchoring portions 102, 104 is greater than the diameter of the filtering portions 106, 108. That is, the diameter of the filter 100 increases from the intermediate region (or from intermediate crimping sleeve 124) towards the proximal end and towards the distal end, thereby forming two reduced diameter filter portions closer to the intermediate region of the filter 100. Viewed another way, two symmetrical portions are provided, each having a filtering portion decreasing in diameter toward the intermediate portion. Since the filtering portions progressively decrease towards the center, the captured blood clots will be directed toward the center of the filter 100 and the center of the blood vessel, thereby enabling it to be more easily dissolved or washed away by the blood flow.

Diameters E1 and E2 in FIG. 10B are taken in one transverse line of the anchoring portion 102 and filtering portion 106, respectively, for an example of how these diameters change. It should be appreciated, that within each portion, the diameters could vary. In a preferred embodiment the diameter of the first and second anchoring portions 102, 104 ranges from about 18 mm to about 30 mm, and the diameter of the first and second filtering portions preferably progressively decreases to about 0.5 mm. Other dimensions are also contemplated.

The compactness of the filter 100 of the present invention can be appreciated by reference to FIGS. 12-13. In the collapsed configuration, the wires 110, 112, and 114 are substantially straight and substantially parallel, i.e. substantially aligned with a longitudinal axis. Adjacent anchoring tubes 140 are axially displaced to minimize the overall diameter of the filter 100. Consequently, the largest diameter of the filter 100 in the collapsed configuration for delivery will be defined by the outer diameter F1 of one of the crimping sleeves, e.g. crimping sleeve 124 of FIG. 12A. The transverse cross sectional view of FIG. 13B shows the dimensional relationship of the anchoring member 140 and wires, with each wire having, by way of example, a diameter of about 0.011 inches to about 0.020 inches, and preferably about 0.012 inches. The crimping sleeve, which circumscribes the three circular cross-sectional wires, is defined by a diameter factor of 2.155, meaning that the inner diameter of the sleeve can be as small as the 2.155 times the wire diameter. Therefore, if the wire diameter is about 0.012 inches, the inner diameter of the crimping sleeve can be about 0.0256 inches (2.155×0.012). If the wall thickness of the sleeve is about 0.010 inches, the outer diameter would be about 0.0456 inches. These dimensions are provided by way of example. The outer diameter of the anchoring tube is preferably selected so that in the collapsed configuration of the filter, the anchoring tube and adjacent wires do not occupy a transverse dimension exceeding the outer diameter of the crimping sleeve, such as shown in FIG. 13B, to maintain the low profile of the filter in the collapsed configuration. Conversely, if the diameter of the anchoring tube is the reference dimension, than the crimping sleeve outer diameter preferably does not exceed the diameter of the anchoring tube and the adjacent wires to maintain the low profile.

FIGS. 12D and 12E illustrate the collapsed configuration of filter 100' of FIG. 10C with a pair of anchoring members 140' on each of the three wires at the distal portion adjacent distal crimping sleeve 122' and at the proximal portion adjacent proximal crimping sleeve 120'.

Like filter 10, filter 100 is preferably made of shape memory metal material, such as Nitinol. Cold saline is injected into the delivery catheter and around the wires 110, 112, 114 in their collapsed position within the delivery catheter to facilitate passage of the wires 110, 112, and 114 through the lumen of the delivery catheter and into the vessel. This shape memory material characteristically exhibits rigidity in the austenitic state and more flexibility in the martensitic state. The cold saline maintains the temperature dependent wires 110, 112 and 114 in a relatively softer condition as they are in the martensitic state within the catheter. This facilitates the exit of wires 12 and 14 from the sheath 210 as frictional contact between the wires 12, 14 and the inner surface of the sheath would otherwise occur if the wires were maintained in a rigid, i.e. austenitic, condition. Once ejected, the filter 100 is warmed by body temperature, causing its transition to its austenitic memorized configuration of FIG. 10A.

Turning now to the methods of insertion of the filter 100, the filter 100 can be inserted through the femoral vein or the right jugular vein and into position in the inferior vena cava, just below the renal arteries. Since the filter 100 is symmetrical, e.g. two filtering portions, it can be loaded into the delivery sheath or catheter in either orientation and inserted in either direction into the inferior vena cava.

One method of insertion of the filter 100 of the present invention is illustrated in FIGS. 14-18. A delivery catheter 200 having a hub 202 is inserted through a leg incision and into the femoral vein "f" of the patient. The delivery catheter 200 is advanced through the iliac arteries into the inferior vena cava just below (upstream with respect to blood flow)) of the renal arteries. Note that the delivery catheter is introduced through an introducer sheath which is not shown for clarity. The introducer sheath is inserted over a guidewire (also not shown) and advanced to the target site. The guidewire is then removed and the delivery catheter is inserted through the lumen in the sheath to the target vessel.

Extending from hub 202 of delivery catheter 200 is tubing 204 and valve assembly 206 to enable saline to be injected into delivery catheter 200 to maintain the softened martensitic state of the vein filter within the catheter 200 so the vein filter is in the substantially straightened configuration as in FIG. 12. A one-way stopcock can be provided to control saline infusion. A metal retaining rod 205 is positioned within the delivery catheter 200 and inserted with the catheter 200.

Once the distal tip 207 of catheter 200 is advanced to the site, i.e. in the inferior vena cava below the renal arteries, the delivery catheter 200 is withdrawn proximally, with rod 205 held in a fixed position to ensure the filter 100 is not pulled back with the catheter 200. Withdrawal of the catheter 200 exposes one of the anchoring portions, e.g. second anchoring portion 104 and one of the filtering portions, e.g. second filtering portion 108, enabling return to the austenitic expanded configuration as the filter is warmed by body temperature (see FIG. 16). Further withdrawal of the delivery catheter 200, releases the other filtering and anchoring portions, e.g. first filter portion 102 and first anchoring portion 106, as shown in FIG. 17. In this position, anchoring tubes 140 engage the vessel wall to retain the filter 100 inside the vessel. The filtering portion 106 will catch blood clots or other small particles to prevent passage to the heart or lungs. FIG. 18A illustrates a blood clot "P" captured in the filtering portion 106 of the filter 100. Note that if the filter 100 was loaded in catheter 200 in the opposite direction, the filtering portion 104 would be upstream of filtering portion 102, when placed within the vessel, and the filtering portion 104 would function to capture blood clots.

FIG. 18B illustrates an alternate embodiment of the vessel filter. The vessel filter is identical to filter 100 of FIG. 18A except that the crimping (connecting) sleeves 422 and 420 are longitudinally offset with respect to central crimping sleeve 424 and with respect to each other. This off centering of the sleeves could reduce turbulence by positioning the obstructions out of alignment. In this embodiment, one or more of the wires 410, 412 and 414 could be of a different length so the sleeves are off-center. As in filter 100, filter 400 has filtering portions 406, 408 and anchoring portions 402, 404, although the filter design is asymmetric.

FIGS. 19 and 20 illustrate the engagement of the anchoring tube with the vessel. In FIG. 19, the surface 145 of tube 140 presses inwardly into the vessel wall, creating an indented region so that ground edges 142 of anchoring tube 140 can press against opposing vessel wall portions "v1" and "v2". This frictional contact retains the filter 100.

In the embodiment of FIG. 20, the engagement of the anchoring tube 40 of FIG. 1 is illustrated. Bevelled edges 44, 46 engage opposing sides "v1" and "v2" of the vessel, formed by the indentation as surface 45 presses against the vessel wall.

In the alternate embodiment of FIG. 25, a series of anchoring tubes 140 on the distal portion and proximal portion of each wire engage the vessel wall.

FIGS. 21-23 illustrate an alternate insertion method through the right internal jugular vein "j". Delivery catheter 200 having a hub 202, a tube 204 and valve assembly 206 for injection of saline is inserted through the right jugular vein, and advanced past the heart and into the inferior vena cava just past the juncture of the renal arteries. The filter 100 is contained within the delivery catheter 200 in the collapsed configuration. The delivery catheter 200 is advanced adjacent the surgical site so that distal tip 20 extends past the juncture of the renal arteries as shown in FIG. 22. The delivery catheter 200 is then retracted, with rod 205 preventing proximal movement of the filter 100, exposing the second filtering portion and second anchoring portion 102 (FIG. 23), allowing it to expand from its straightened configuration to its austenitic expanded configuration as it is warmed by body temperature. Further withdrawal of the delivery catheter 200 in the direction of the arrow will release the first anchoring portion 104 and the first filtering portion 108, allowing expansion against the wall of the vessel, to the position of FIG. 18A. Blood clots could then be captured in filtering portion 106.

As can be appreciated, the filter 100 can be inserted into the inferior vena cava in either orientation since once expanded, the upstream filtering portion will capture blood clots and the two anchoring portions will help retain the filter 100 anchored and centered in the vessel.

FIG. 24 illustrates another alternate method of insertion wherein the delivery catheter 200 is inserted directly into the superior vena cava "s" and advanced into the inferior vena cava in the same manner as described in FIGS. 22 and 23.

The other embodiments of the filters, i.e. filters 10, 60, and 80, can be inserted through the femoral vein, jugular vein, superior vena cava, etc. in a similar manner as described above for filter 100.

In the foregoing embodiments, preferably, the filter is released by withdrawal of the delivery catheter as described. However, alternatively, the filter can be released by pushing or advancing the filter from the delivery catheter. Additionally, release can be achieved by a combination of withdrawal of the catheter and advancement of the filter.

It should also be appreciated that that the terms proximal and distal for filter 100 (as well as for the other filters, e.g. filters 100' and 100") are utilized for convenience for orientation purposes, since the filter 100 can be inserted in either orientation.

The filter 100 (and 100') can, if desired, be withdrawn intravascularly. The filter does not require any additional components for removal from the vessel. The filter can simply be grasped by one or more of the wires. The filter can alternatively be grasped for removal at either the proximal crimping sleeve 120 or the distal crimping sleeve 122 which, as described above, retains the three wires. Due to the configuration of the filter, and particularly the symmetrical anchoring and filtering portions, the filter 100 (and 100') can be removed from either end regardless of the direction in which it is inserted. That is, a filter removal tool can be inserted through either the internal jugular vein (or superior vena cava) or through the femoral vein to access the filter positioned in the inferior vena cava. The filter removal instrument engages the filter wires or crimping sleeve, and applies an axial force to the filter to collapse the filter, disengage the anchoring members, and withdraw it through the vein in which the removal instrument was initially inserted.

Turning now to removal of the vein filter, FIGS. 25 and 30-33 illustrate several different instruments for removing vessel filter 100. (Vessel filter 100' would be removed in the same manner). FIGS. 26-29 illustrate different instruments for removing vessel filters having welded wire ends.

With reference first to FIG. 25, a removal tool 300 (only the distal portion is shown) has a flexible shaft 301 and three elongated wire engaging members 302, 304, and 306 extending therefrom. The wire engaging members 302, 304, and 306 each have a lateral slot 312, 314, 316, respectively, to engage one of the wires 110, 112, and 114.

In use, the tool 300 is inserted through the internal jugular vein with the wire engaging members 302, 304, 306 retracted within shaft 301. Once positioned adjacent the implanted filter 100, the members 302, 304 and 306 are advanced from the shaft 301 and manipulated so that the lateral slots 312, 314 and 316 engage the respective wire of the second anchoring portion 104. Preferably, the engaging members 302, 304, and 306 are manipulated individually. Once the wires 110, 112 and 114 are engaged, the tool 300 is pulled in the opposite direction of insertion, i.e. a longitudinal force is applied in the direction of the arrow, thereby applying an axial pulling force on the filter 100. As the force is applied, the filter collapses as the wires are pulled toward a straightened position and the anchoring members 140 disengage from the vessel wall without causing trauma to the wall. The filter wires 110, 112 and 114 are pulled inside hollow shaft 301 to a more straightened position and the filter is removed from the vessel wall.

Although tool 300 is shown from an internal jugular (or superior vena cava) approach, alternatively the tool 300 can be inserted through the femoral vein. In this approach, the tool operates in the identical fashion except that it would engage wires 110, 112, 114 in the first anchoring portion 102 and withdraw the filter 100 through the femoral vein.

The wire engaging members 302, 304, and 306 are described as slidable within the shaft 301 to pull the filter 100 within the shaft 301. It is also contemplated that the wire engaging members 302, 304 and 306 can be fixedly attached to shaft 301, and the shaft 301 positioned within a catheter (not shown). In this version, the shaft and wire engaging members would be inserted into the vessel with the engaging members withdrawn inside the catheter, and subsequently advanced relative to the catheter so that the engaging members protrude therefrom to engage the wires. The filter 100 would then be pulled along with the engaging members and shaft within the catheter for removal from the vessel.

In an alternate embodiment, instead of slotted hooks, a grasper can be utilized. In this embodiment, the removal tool has three graspers which would be inserted through shaft 301. The graspers would have either one of the jaws or both jaws movable between an open position and a closed clamping position to grasp the respective wire. That is, each pair of jaws, in the open position, would be placed around one of the respective wires 110, 112, 114, and the jaws would be manipulated, preferably individually, from the proximal end of the tool to close the jaws around the respective wire. The jaws can be configured in a similar configuration as that described below with respect to FIG. 30. Once firmly grasped, the tool would be pulled in the opposite direction of insertion to disengage and withdraw the filter. The tool (graspers) can be inserted in either direction, i.e. femoral access or internal jugular/vena cava access. The graspers can be withdrawn within shaft 301, or alternatively, as explained with respect to the aforedescribed embodiment, the graspers and shaft can be placed inside a catheter and moved relative to the catheter. The filter would thus be withdrawn with the graspers and shaft into the catheter for removal from the vessel.

FIGS. 26A and 26B illustrate an alternate embodiment of a removal tool, designated by reference numeral 340, used to remove the filter having wire ends welded together instead of a crimping sleeve as described above. The filter 100" (only the distal end is shown) terminates in wires 110", 112", and 114" welded together to form welded end 101". Filter removal tool 340 (only the distal end is shown) has a series of flexible barbs 342 extending from the interior surface 344 of wall 345 into lumen 346. Removal tool 340 is inserted over welded end 101" to engage the wires. The barbs 342 are oriented to allow advancement of the wires within lumen 346 in the direction of the arrow, but prevent movement of the wires in the opposite direction. Thus, the wires are firmly locked within the tool 340 and the tool can be pulled in the direction opposite its insertion direction to pull and collapse the filter to remove it from the vessel.

FIGS. 27A and 27B illustrate an alternate embodiment of a removal tool for removing filter 100". Removal tool 360 (only the distal end is shown) has a tubular braided structure 362 within tube 364 which is movable between an expanded and a collapsed position. The braided structure 362 is placed over the welded end 101" in the expanded position, and then pulled in the direction of the arrow of FIG. 27A to collapse the braided structure 362 radially inwardly around welded end 101" (see direction of arrows of FIG. 27A) to frictionally engage the wires 110", 112", 114" to remove the filter 100". The filter 100" is then removed with the tubular braid 362 through lumen 365 of tool 360.

In the embodiment of FIG. 28, the removal tool 380 has a hook 382 which is slidable to engage the wires of the filter 100" just below the welded region 101". Retraction of the hook 382 pulls the filter 100" into inner tube 383. Inner tube 383 is positioned within tube 385.

In the embodiment of FIG. 29, a spring biased finger 392 is attached to the wall 391 of removal tool 390 by a pin 394. The welded end 101" of vein filter 100" is retained in the tool 390 by the engagement of finger 392 just below the welded region 101".

FIGS. 30-33 illustrate an alternate approach to removing the vessel filter wherein the wire retaining sleeve, e.g. the crimping sleeve, is engaged by the filter removal tool. In one embodiment as shown in FIG. 30, a grasper 400 (only the distal portion is shown) having a flexible hollow shaft 401 and a pair of jaws 404, 406 are inserted to the inferior vena cava from an internal jugular or superior vena approach. Jaws 404, 406 extend from shaft 401 and are movable from an open position to a closed position to grasp distal retaining sleeve 122. Alternatively, one jaw can be fixed and the other jaw moved relative to the fixed jaw between an open and closed position.

Once the crimping sleeve 122 is grasped by jaws 404, 406, the jaws are pulled in the direction of the arrow (opposite the direction of insertion) to apply an axial force on the filter 100 to collapse the filter and disengage the anchoring members 140 from the vessel wall. The filter 100 moves toward a collapsed straightened position and is pulled by the jaws 404, 406 inside the flexible shaft 401 as the jaws are retracted within the shaft 401 to remove the filter therethrough. As with the aforedescribed embodiments, alternatively the grasper 400 can be placed within a catheter for slidable movement therein and the filter 100 withdrawn through the catheter as the jaws and shaft are retracted therein.

FIG. 30 illustrates the tool 400 grasping distal crimping sleeve 122. It is also contemplated that the tool 400 can alternatively be inserted through the femoral vein to grasp proximal crimping sleeve 120 for removal of the filter 100 through the femoral vein.

FIG. 31 illustrates another embodiment of a filter removal tool (only a distal portion is shown), designated generally by reference numeral 500, in the form of a snare having a wire 502 extending from flexible shaft 501. The snare wire 502 is inserted from an internal jugular (or superior vena cava) approach to access the filter 100 implanted within the inferior vena cava. The wire 502 is placed adjacent the edge of the distal crimping sleeve 122, and tightened to close the loop against the crimping sleeve edge by applying tension at a proximal end to firmly engage the filter 100. The filter 100 is then collapsed and the anchoring members 140 disengaged as the snare pulls the filter either through shaft 501 as wire 502 is retracted within shaft 501 or through a catheter (not shown) along with the shaft 501 for removal of the filter 100 in the direction of the arrow.

FIG. 32 illustrates a femoral approach to the filter 100. As shown, wire 502 of snare 500 is placed adjacent the edge of the proximal crimping sleeve 120 and tensioned to grasp the filter 100. The filter 100 would then be removed in the direction of the arrow, i.e. through the femoral vein.

FIGS. 33A and 33B show an alternate instrument for removing vein filter 100 by engagement of the crimping sleeve. Removal instrument 600 has an outer tube 608, an inner tube 607, and a hook 602 extending through lumen 604 in wall 606 of tube 607. Hook 602 is advanced through lumen 604 to engage the edge of distal crimping sleeve 122. The hook is preferably slidable within lumen 604 to pull sleeve within lumen 605, and the instrument 600 and filter are retracted within a sheath.

FIGS. 34 and 35 illustrate alternate embodiments of the vein filter having an atraumatic tip. In FIG. 34, filter wires 810, 812, and 814 of filter 800 (only the distal end is shown) terminate in a spring tip 815 similar to atraumatic spring tips found in guidewires. In FIG. 35, the filter 850 (only the distal end is shown) terminates in a ball tip 852. Such atraumatic tipped filters can be removed in similar fashions as those described above, e.g. grasping the individual wires or the tip by graspers, a snare, hook, etc. The vein filter of FIG. 35 could further be removed by a collet 702 as shown in FIGS. 36A and 36B. Collet 702 of removal instrument 700 is opened as it is advanced past wall 704 to create an opening 706 for ball tip 852. Once the ball tip 852 is grasped, collet 702 is pulled back into housing 705 in the direction of the arrow in FIG. 36C, with walls 704 camming the collet to the closed position of FIG. 36C.

FIG. 37 illustrates yet another embodiment of the vein filter, designated by reference numeral 900, having a circumferential recess or indentation 905 formed in the welded region 915 of the wires 910, 912 and 914. A snare or other grasping tool can be placed in the recess and utilized to grasp and remove the filter. An indentation 905 can also be formed in a welded region at the opposite end of the filter 900.

The foregoing removal tools can also be utilized to reposition the vein filter rather than remove (retrieve) it. The tools would be inserted and would function to grasp the filter in a similar manner as described above, but rather than remove the filter, it would move it within the vessel and then release it. The tool would then be removed, leaving the vein filter in place.

While the above description contains many specifics, those specifics should not be construed as limitations on the scope of the disclosure, but merely as exemplifications of preferred embodiments thereof. For example the dimensions of the components have been provided by way of example and other dimensions are contemplated. Also, although filter embodiments utilizing one, two or three wires are described, additional wires can be utilized to form the filter or fewer than the two or three wires can be used to form the respective filter. Additionally, the filter can be inserted in other regions of the body besides the inferior vena cava. Those skilled in the art will envision many other possible variations that are within the scope and spirit of the disclosure as defined by the claims appended hereto.

What is claimed is:

1. A method of implanting and subsequently removing a vein filter in the inferior vena cava of a patient comprising:
   inserting through a vessel in either a first direction or a second direction a catheter having a filter positioned therein in a collapsed configuration so that wire sections of the filter are in a substantially elongated configuration, the filter having a center, a central longitudinal axis, a distalmost end and a proximalmost end;
   releasing the filter from the catheter to enable the filter to move to an expanded configuration, in the expanded configuration first and second mounting portions expand to a first diameter and first and second filter portions expand to a second smaller diameter, each of the filter portions being longitudinally axially spaced from each of the mounting portions and each filter portion expanding on opposing sides of the central longitudinal axis, the first filter portion being closer to the proximalmost end of the filter than the second filter portion and the first mounting portion being at the proximalmost end of the filter, the first mounting portion expanding on opposing sides of the central longitudinal axis with the first filter portion being closer to a center than the first mounting portion, and the first filter portion being closer to the proximalmost end of the filter than the second filter portion such that the first filter portion is positioned between the proximalmost end and the second filter portion, and the second mounting portion expanding on opposing sides of the central longitudinal axis and being at a distalmost end of the filter with the second filter portion being closer to the center then the second mounting portion such that the second filter portion is positioned between the distalmost end and the first filter portion, and the first and second filter portions being positioned adjacent the center and converging toward each other adjacent the center at a converging region and the first and second mounting portions being positioned further from the center, the wire sections converging at a proximal end and at a distal end of the filter so the mounting portions each terminate in a converged end, and the wire sections including a plurality of wires forming a series of loops having axially spaced apexes in the mounting portions and a series of loops having axially spaced apexes in the filter portions, the loops in the filter portions being axially spaced from the converging region;
   leaving the filter in the vessel for a period of time;
   inserting after the period of time in either the first direction or the second direction a single filter removal tool to engage at least one of the wire sections which form part of the mounting portions; and moving the tool in a direction opposite the insertion direction of the tool to move the filter towards the collapsed configuration and to remove the entire filter in the second direction.

2. The method of claim 1, wherein the filter is inserted through the internal jugular vein and removed through either the internal jugular vein or the femoral vein.

3. The method of claim 1, wherein the filter is inserted through the femoral vein and removed through either the internal jugular vein or the femoral vein.

4. The method of claim 1, further comprising the step of delivering cold saline into the catheter to maintain the filter in the collapsed configuration.

5. A method of claim 1, wherein the step of releasing the filter comprises withdrawing the catheter to expose the filter.

6. The method of claim 1, wherein the filter terminates in an atraumatic tip and the step of inserting the tool to engage at least one of the wire sections comprises the step of engaging the atraumatic tip.

7. The method of claim 1, wherein the filter removal tool comprises a snare, and the method of inserting the tool includes inserting the tool to engage a retaining sleeve of the filter, and the method further comprises the step of tightening the snare against the retaining sleeve of the filter.

8. The method of claim 1, wherein the mounting and filter portions are formed by closed looped portions of varying transverse dimensions.

9. A method of implanting and subsequently removing a vein filter in the inferior vena cava of a patient comprising:

inserting through a vessel a catheter having a filter positioned therein in a collapsed configuration so that wire sections of the filter are in a substantially elongated configuration, the wire sections converging and held at a proximal portion by a proximal retaining sleeve, converging and held at a distal portion by a distal retaining sleeve and converging at a center portion at a central retaining sleeve, the filter having a proximal portion and a distal portion, a central longitudinal axis and a center between the proximal and distal portions;

releasing the filter from the catheter to enable the filter to move to an expanded configuration, in the expanded configuration first and second mounting portions expand to a first diameter and first and second filter portions expand to a second smaller diameter, each of the filter portions being longitudinally axially spaced from each of the mounting portions, the first filter portion being closer to a proximalmost end than the second filter portion and the first mounting portion being at the proximalmost end of the filter with the first filter portion being closer to the center of the filter than the first mounting portion, and the first filter portion being closer to the proximalmost end than the second filter portion such that the first filter portion is positioned between the proximalmost end and the second filter portion and the second mounting portion being at the distalmost end of the filter with the second filter portion being closer to the center than the second mounting portion, and the second filter portion being closer to the distalmost end than the first filter portion such that the second filter portion is positioned between the distalmost end and the first filter portion, the mounting and filter portions formed by looped portions of varying transverse dimensions in an axial direction, the looped portions formed by a plurality of wires forming a series of loops having axially spaced apexes in the mounting portions and a series of loops having axially spaced apexes in the filter portions, the loops in the filter portions are axially spaced from the central retaining sleeve so the loops in the first filter portion are positioned between the central retaining sleeve and the proximalmost end and the loops in the second filter portion are positioned between the central retaining sleeve and the distalmost end, the first mounting portion converging at the proximal portion into the proximal retaining sleeve and the second mounting portion converging at the distal portion into the distal retaining sleeve, and the filter portions converging adjacent the center into the central retaining sleeve;

leaving the filter in the vessel for a period of time;

inserting a single filter removal tool in a first direction after a period of time to engage one of the retaining sleeves; and moving the single removal tool in a second direction opposite the first insertion direction of the tool to move the filter towards the collapsed configuration and to remove the entire filter in the second direction.

10. The method of claim 9, wherein the filter is inserted through the internal jugular vein and removed through either the internal jugular vein or the femoral vein.

11. The method of claim 9, wherein the filter is inserted through the femoral vein and removed through either the internal jugular vein or the femoral vein.

12. The method of claim 9, further comprising the step of delivering cold saline into the catheter to maintain the filter in the collapsed configuration.

13. The method of claim 9, wherein the filter removal tool comprises a snare, and the method of inserting the tool to engage the retaining sleeve further comprises the step of tightening the snare against the retaining sleeve of the filter.

14. The method of claim 9, wherein the proximal sleeve is positioned at a proximalmost end of the filter and the distal sleeve is positioned at a distalmost end of the filter.

15. The method of claim 9, wherein the filter has a central longitudinal axis and each of the filter portions and each of the mounting portions expand to opposing sides of the central longitudinal axis.

* * * * *